United States Patent
Hafez

(10) Patent No.: US 9,765,367 B2
(45) Date of Patent: Sep. 19, 2017

(54) METHOD AND SYSTEM FOR PRODUCTION OF HYDROGEN, METHANE, VOLATILE FATTY ACIDS, AND ALCOHOLS FROM ORGANIC MATERIAL

(71) Applicant: GREENFIELD SPECIALTY ALCOHOLS INC., Toronto (CA)

(72) Inventor: Hisham Mohamed Hafez, London (CA)

(73) Assignee: GREENFIELD SPECIALTY ALCOHOLS INC., Toronto (CA)

( * ) Notice: Subject to any disclaimer, the term of this patent is extended or adjusted under 35 U.S.C. 154(b) by 0 days.

(21) Appl. No.: 14/907,475

(22) PCT Filed: Jul. 25, 2014

(86) PCT No.: PCT/CA2014/000600
§ 371 (c)(1),
(2) Date: Jan. 25, 2016

(87) PCT Pub. No.: WO2015/010192
PCT Pub. Date: Jan. 29, 2015

(65) Prior Publication Data
US 2016/0186218 A1    Jun. 30, 2016

Related U.S. Application Data

(60) Provisional application No. 61/858,708, filed on Jul. 26, 2013.

(51) Int. Cl.
C12P 7/04 (2006.01)
C12P 7/64 (2006.01)
(Continued)

(52) U.S. Cl.
CPC .......... *C12P 7/6409* (2013.01); *C02F 3/2813* (2013.01); *C12F 3/02* (2013.01);
(Continued)

(58) Field of Classification Search
CPC .................. C12P 7/04; C12P 5/023
See application file for complete search history.

(56) References Cited

U.S. PATENT DOCUMENTS

| 3,649,516 A | 3/1972 | Cole, Jr. et al. |
| 4,491,522 A | 1/1985 | Ishida et al. |

(Continued)

FOREIGN PATENT DOCUMENTS

| CA | 2751046 A1 | 8/2010 |
| CA | 2786751 A1 | 7/2011 |

(Continued)

OTHER PUBLICATIONS

European Patent Application No. 13749197.3-1501 Supplementary Search Report dated Sep. 17, 2015.
(Continued)

*Primary Examiner* — Rosanne Kosson
(74) *Attorney, Agent, or Firm* — Borden Ladner Gervais LLP

(57) ABSTRACT

A method for producing $H_2$, methane, VFAs and alcohols from organic material, including the steps of introducing organic material and microorganisms into a completely mixed bioreactor for producing $H_2$, $CO_2$, VFAs, and alcohols; recovering H2 and CO2; recovering a first liquid effluent including microorganisms, VFAs, and alcohols; introducing the first liquid effluent into a gravity settler for separating into a first biomass including microorganisms and a second liquid effluent including VFAs, alcohols and microorganisms; introducing the second liquid effluent into a separation module for separating into a second biomass including microorganisms and a third liquid effluent including VFAs and alcohols; recovering at least a portion of the third liquid effluent; and providing a recovered biomass by recovering at least a portion of the first biomass, the second
(Continued)

biomass, or both, and introducing the recovered biomass into a biomethanator for production of $CH_4$ and $CO_2$.

8 Claims, 17 Drawing Sheets

(51) Int. Cl.

| | |
|---|---|
| C12F 3/02 | (2006.01) |
| C12P 3/00 | (2006.01) |
| C12P 5/02 | (2006.01) |
| C12P 7/40 | (2006.01) |
| C02F 3/28 | (2006.01) |
| C12M 1/00 | (2006.01) |
| C12M 1/34 | (2006.01) |
| C12P 7/08 | (2006.01) |
| C12P 7/16 | (2006.01) |
| C12P 7/28 | (2006.01) |
| C02F 3/34 | (2006.01) |
| C12P 39/00 | (2006.01) |

(52) U.S. Cl.
CPC ............ *C12M 23/58* (2013.01); *C12M 29/00* (2013.01); *C12M 41/12* (2013.01); *C12M 41/26* (2013.01); *C12M 47/10* (2013.01); *C12P 3/00* (2013.01); *C12P 5/023* (2013.01); *C12P 7/04* (2013.01); *C12P 7/08* (2013.01); *C12P 7/16* (2013.01); *C12P 7/28* (2013.01); *C12P 7/40* (2013.01); *C02F 3/34* (2013.01); *C12P 39/00* (2013.01); *Y02E 50/17* (2013.01); *Y02E 50/343* (2013.01)

(56) References Cited

U.S. PATENT DOCUMENTS

| | | | |
|---|---|---|---|
| 5,855,764 | A | 1/1999 | Greaney et al. |
| 7,439,047 | B2 | 10/2008 | Rozendal et al. |
| 2005/0194311 | A1 | 9/2005 | Rozich |
| 2008/0197074 | A1 | 8/2008 | Gallagher et al. |
| 2009/0317882 | A1 | 12/2009 | Cheng et al. |
| 2009/0325255 | A1 | 12/2009 | Chakravarti et al. |
| 2011/0011799 | A1 | 1/2011 | Rozendal et al. |
| 2011/0159559 | A1* | 6/2011 | Claassen .................. C12N 1/20 435/160 |
| 2011/0236946 | A1 | 9/2011 | Maclachlan et al. |

FOREIGN PATENT DOCUMENTS

| | | | |
|---|---|---|---|
| CN | 1856706 | A | 11/2006 |
| CN | 102300977 | A | 12/2011 |
| WO | 2005005981 | A2 | 1/2005 |
| WO | 2009034439 | A2 | 3/2009 |
| WO | 2010056460 | A2 | 5/2010 |
| WO | 2010085893 | A1 | 8/2010 |

OTHER PUBLICATIONS

U.S. Appl. No. 14/518,307 Final Office Action dated Oct. 12, 2016.
International Preliminary Report on Patentability for International Patent Application No. PCT/CA2014/051011, mailed on Apr. 26, 2016, 8 pages.
Vavilin et al., "Methanosarcina as the Dominant Aceticlastic Methanogens During Mesophilic Anaerobic Digestion of Putrescible Waste", Antonie van Leeuwenhoek, Nov. 2008, vol. 94 (4), pp. 593-605.
Written Opinion for International Patent Application No. PCT/CA2014/000600, mailed on Oct. 17, 2014, 8 pages.
Written Opinion for International Application No. PCT/CA2014/051011, mailed on Jan. 16, 2015, 7 pages.
European Patent Application No. 14829514, Supplementary European Search Report dated Feb. 27, 2017.
Chinese Patent Application No. 201380019493.7, Office Action dated Oct. 26, 2016 with English summary, English summary only; Examiner cannot read Chinese.
Azbar et al., "State of the Art Progress in Production of Biohydrogen", Bentham Science Publishers, Jun. 7, 2012, 262 pages.
Bankar et al., "Continuous two stage acetone—butanol—ethanol fermentation with integrated solvent removal using Clostridium acetobutylicum B 5313", Bioresource Technology, 2012, available online Dec. 8, 2011, vol. 106, pp. 110-116.
Chang et al., "Biohydrogen production with fixed-bed bioreactors", International Journal of Hydrogen Energy, vol. 27, Issues 11-12, Nov.-Dec. 2002, pp. 1167-1174.
Das et al., "Recent Developments in Biological Hydrogen Production Processes", Chemical Industry & Chemical Engineering Quarterly, vol. 14, No. 2, accepted for publication Mar. 25, 2008, published 2008, pp. 57-67.
Dayton et al., "Fuel Cell Integration—A Study of the Impacts of Gas Quality and Impurities", Chemistry of Bioengergy Systems Division of the National Bioenergy Centre, Milestone Completion Report, National Renewable Energy Laboratory, accepted for publication Jul. 7, 2001, 28 pages.
Fang et al., "Effect of pH on hydrogen production from glucose by a mixed culture", Bioresource Technology, vol. 82, Mar. 2002, pp. 87-93.
Gomez et al., "Hydrogen production: two stage processes for waste degradation", Bioresource Technology, vol. 102, No. 18, Sep. 2011, pp. 8621-8627.
Hafez et al. "Biological Hydrogen Production from Corn-Syrup Waste Using a Novel System", Energies, vol. 2, Jun. 24, 2009, pp. 445-455.
Hafez et al., "Effect of organic loading on a novel hydrogen bioreactor", International Journal of Hydrogen Energy, vol. 35, 2010, available online Nov. 10, 2009, pp. 81-92.
Hawkes et al., "Sustainable fermentative hydrogen production: challenges for process optimization", International Journal of Hydrogen Energy, vol. 27, issues 11-12, Nov.-Dec. 2002, pp. 1339-1347.
Horiuchi et al., "Selective production of organic acids in anaerobic acid reactor by pH control", Bioresource Technology, vol. 82, Issue 3, May 2002, pp. 209-213.
Hussy et al. "Continuous fermentative hydrogen production from sucrose and sugarbeet", International Journal of Hydrogen Energy, vol. 30, issue 5, 2005, Apr. 2005, pp. 471-483.
International Patent Application No. PCT/CA2013/050121, International Search Report and Written Opinion dated Apr. 18, 2013.
International Patent Application No. PCT/CA2013/050121, Chapter II International Preliminary Report on Patentability, dated Mar. 3, 2014.
Jackson et al. "Anaerobic microbial metabolism can proceed close to thermodynamic limits", Nature, vol. 415, Jan. 24, 2002, pp. 454-456.
Kim et al. "Effect of gas sparging on continuous fermentative hydrogen production", International Journal of Hydrogen Energy, vol. 31, issue 15, Dec. 2006, pp. 2158-2169.
Kraemer et al. "Improving the yield from fermentative hydrogen production", Biotechnology Letters, vol. 28, Issue 5, May 2007, pp. 685-695.
Lee et al., "Biological hydrogen production: prospects and challenges", Trends Biotechnology, vol. 28, No. 5, May 2010, pp. 262-271.
Levin et al. "Biohydrogen production: prospects and limitations to practical application", International Journal of Hydrogen Energy, vol. 29, issue 2, Feb. 2004, pp. 173-185.
Li et al., "Fermentative Hydrogen Production from Wastewater and Solid Wastes by Mixed Cultures", Critical Reviews in Environmental Science and Technology, vol. 37, No. 1, published online Jan. 12, 2007, pp. 1-39.

(56) References Cited

OTHER PUBLICATIONS

Liang et al., "Behavioral study on hydrogen fermentation reactor installed with silicone rubber membrane", International Journal of Hydrogen Energy, vol. 27, vol. 11-12, Nov.-Dec. 2002, pp. 1157-1165.

Liu et al., "Electrochemically Assisted Microbial Production of Hydrogen from Acetate", Environmental Science & Technology, vol. 39, No. 11, Apr. 22, 2005, pp. 4317-4320.

Mandal et al., "Improvement of biohydrogen production under decreased partial pressure of H2 by Enterobacter cloacae", Biotechnology Letters, vol. 28, issue 11, published online Jun. 2, 2006, pp. 831-835.

Matsunaga et al., "Microaerobic Hydrogen Production by Photosythetic Bacteria in a Double-Phase Photobioreactor", Biotechnology and Bioengineering, vol. 68, No. 6, Jun. 20, 2000, pp. 647-651.

Nath et al., "Improvement of fermentative hydrogen production: various approaches", Appl Microbiol Biotechnol, vol. 65, Oct. 2004, pp. 520-529.

O-Thong et al., "Evaluation of methods for preparing hydrogen-producing seed inocula under thermophilic condition by process performance and microbial community analysis", Bioresource Technology, vol. 100, 2009, available online Sep. 2, 2008, pp. 909-918.

Park et al., "Removal of Headspace CO2 Increases Biological Hydrogen Production", Environmental Science & Technology, vol. 39, No. 12, published online May 5, 2005, pp. 4416-4420.

Rozendal et al., "Principle and perspectives of hydrogen production through biocatalyzed electrolysis", International Journal of Hydrogen Energy, vol. 31, issue 12, Sep. 2006, pp. 1632-1640.

Show et al., "Critical assessment of anaerobic processes for continuous biohydrogen production from organic wastewater", International Journal of Hydrogen Energy, vol. 35, issue 24, Dec. 2010, pp. 13350-13355.

Show et al., "Production of hydrogen in a granular sludge-based anaerobic continuous stirred tank reactor", International Journal of Hydrogen Energy, vol. 32, issue 18, Dec. 2007, pp. 4744-4753.

Tanisho et al., "Effect of CO2 Removal on Hydrogen Production By Fermentation", International Journal of Hydrogen Energy, vol. 23, No. 7, Jul. 1998, pp. 559-563.

Vallero et al., "High rate sulfate reduction in a submerged anaerobic membrane bioreactor (SAMBaR) at high salinity", Journal of Membrane Science, vol. 253, issue 1-2, May 5, 2005, pp. 217-232.

Vavilin et al., "Modelling Hydrogen Partial Pressure Change as a Result of Competition Between the Butyric and Propionic Groups of Acidogenic Bacteria", Bioresource Technology, vol. 54, issue 2, accepted for publication Aug. 26, 1995, pp. 171-177.

Villano et al., "Perspectives of biofuels production from renewable resources with bioelectrochemical systems", Asia-Pacific Journal of Chemical Engineering, vol. 7, No. suppl. S3, Aug. 2012, pp. S263-S274.

Wu et al., "HRT-dependent hydrogen production and bacterial community structure of mixed anaerobic microflora in suspended, granular and immobilized sludge systems using glucose as the carbon substrate", International Journal of Hydrogen Energy, vol. 33, issue 5, Mar. 2008, pp. 1542-1549.

Zhang et al. "Effect of hydraulic retention time on biohydrogen production and anaerobic microbial community", Process Biochemistry, vol. 41, issue 10, Oct. 2006, pp. 2118-2123.

Zhang et al., "Rapid Formation of Hydrogen-Producing Granules in an Anaerobic Continuous Stirred Tank Reactor Induced by Acid Incubation", Biotechnology and Bioengineering, vol. 96, No. 6, Apr. 15, 2007, pp. 1040-1050.

Zhang et al., "The role of acid incubation in rapid immobilization of hydrogen-producing culture in anaerobic upflow column reactors", International Journal of Hydrogen Energy, vol. 33, issue 19, Oct. 2008, pp. 5151-5160.

Zhang et al., "Biological hydrogen production by Clostridium acetobutylicum in an unsaturated flow reactor", Water Research, vol. 40, issue 4, Feb. 2006, pp. 728-734.

Zverlov et al., "Bacterial acetone and butanol production by industrial fermentation in the Soviet Union: use of hydrolyzed agricultural waste for biorefinery", Appl Microbiol Biotechnol, vol. 71, issue 5, first online May 10, 2006, pp. 587-597.

International Patent Application No. PCT/CA2014/000600, International Search Report dated Oct. 17, 2014.

Hafez, "Two-stage Anaerobic Digestion Process for H2 and CH4 Production from High Strength Industrial Organic Streams", Canadian Biogas Conference [online], retrieved from Internet http://www.gtmconference.ca/site/index.php/20 14-presentations/doc down1oad3-9d/451-20 130b3d-hafez>, May 2013, 8 pages.

International Patent Application No. PCT/CA2014/051011, International Search Report dated Jan. 16, 2015.

NASR, "C02 Sequestration: Effect on biohydrogen production and microbial community in the integrated biohydrogen reactor clarifier system (IBRCS)", Advanced Biofuels Symposium Poster Session Project No. 75, Ottawa Ontario, retrieved from the internet: http://www.biofuelnetca/wp-conlent/uploads/20 14/05/roster-session Abstracts I.pdf, May 27-29, 2014, 2 pages.

El-Naggar, "The Integrated Biohydrogen Reactor Clarifier System (IBRCS): Setup, Performance, and Application", Wastewater & Biosolids Treatment & Reuse: Bridging Modeling and Experimental Studies, Dr. Domenico Santoro, Trojan Technologies and Western University Eds, ECI Symposium Series, retrieved from the internet:http://dc.engconfintl.org/cgi/viewcontent.cgi?article=I 0 15&context=wbtr _i, Jun. 8-14, 2014, pp. 1-28.

Hawkes et al., "Continuous dark fermentative hydrogen production by mesophilic microflora: Principles and progress", International Journal of Hydrogen Energy, vol. 32, issue 2, Feb. 2007, pp. 172-184.

European Patent Application No. 13749197.3 Supplementary Search Report dated Aug. 31, 2015.

Wang et al., "Integrated hydrogen production process from cellulose by combining dark fermentation, microbial fuel cells, and microbial electrolysis cell", Bioresource Technology, vol. 102, issue 5, Mar. 2011, pp. 4137-4143.

Lalaurette et al., "Hydrogen production from cellulose in a two-stage process combining fermentation and electrohydrogenesis", International Journal of Hydrogen Energy, vol. 34, issue 15, Aug. 2009, pp. 6201-6210.

Lu et al. "Hydrogen production with effluent from an ethanol-H2-coproducing fermentation reactor using a single-chamber microbial electrolysis cell", Biosensors and Bioelectronics, vol. 24, issue 10, Jun. 15, 2009, pp. 3055-3060.

U.S. Appl. No. 13/768,449, Office Action dated Sep. 16, 2015.
U.S. Appl. No. 14/518,307, Office Action dated Feb. 23, 2016.
U.S. Appl. No. 14/518,307, Office Action dated Sep. 4, 2015.
International Patent Application No. PCT/CA2014/000600, International Preliminary Report on Patentability dated Nov. 20, 2015.
European Patent Application No. 14855028.8, Extented European Search Report dated Apr. 25, 2017.

Guo et al., "Enhancement of Butanol Production and Reducing Power Using a Two-stage Controlled-ph Strategy in Batch Culture of *Clostridium Acetobutylicum* XY16," World Journal of Microbiology and Biotechnology, Jul. 2012, vol. 28 (7), pp. 2551-2558.

Hazef et al., "Biological Hydrogen Production from Corn-Syrup Waste Using a Novel System," Energies, Jun. 24, 2009, vol. 2(2), pp. 445-455.

* cited by examiner

METHOD AND SYSTEM FOR PRODUCTION OF HYDROGEN, METHANE, VOLATILE FATTY ACIDS, AND ALCOHOLS FROM ORGANIC MATERIAL

CROSS REFERENCE TO RELATED APPLICATIONS

This application is a National Stage of International Application No. PCT/CA2014/000600, filed Jul. 25, 2014, which claims priority to U.S. Provisional Patent Application No. 61/858,708, filed on Jul. 26, 2013, the entire contents of which are incorporated herein by reference.

FIELD

The present disclosure relates to the production of hydrogen, methane, volatile fatty acids, and alcohols. More particularly, the present disclosure relates to the treatment of organic material with microorganisms for the production of hydrogen, methane, volatile fatty acids, and alcohols.

BACKGROUND

The problems of soaring energy demand and environmental pollution are addressed by various biological processes for the treatment of industrial wastes. Biohydrogen production through dark fermentation is one known process for the treatment of industrial waste and production of hydrogen.

Microorganisms are capable of producing hydrogen via either photosynthesis or preferably through fermentation (Matsunaga, T., Hatano, T., Yamada, A., Matsumoto, M., (2000) Microaerobic hydrogen production by photosynthetic bacteria in a double phase photobioreactor. *Biotechnol. Bioeng.* 68 (6), 647-651). Organic pollutants are anaerobically converted to methane in two distinct stages: acidification and methanogenesis. Acidification produces hydrogen as a by-product which in turn is used as an electron donor by many methanogens at the second stage of the process (Fang, H. H. P. and Liu, H. (2002) Effect of pH on hydrogen production from glucose by a mixed culture. *Bioresource Technology* 82, 87-93). Separation of the two stages is feasible for hydrogen collection from the first stage. The second stage is further used for treatment of the remaining acidification products, which includes mainly volatile fatty acids (VFAs).

The continuously stirred tank reactor (CSTR) has been the most widely used system for continuous hydrogen production (Li, C., Fang, H. H. P., (2007) Fermentative hydrogen production from wastewater and solid wastes by mixed cultures. *Critical reviews in Env. Sci. and Tech.,* 37, 1-39). Since in a CSTR biomass solids residence time (SRT) is the same as the hydraulic retention time (HRT), its concentration in the mixed liquor is highly affected by the recommended HRT of 1-12 h which is optimal for high hydrogen production rates (Li and Fang, 2007). The maximum specific growth rate ($\mu max$) for mixed culture of 0.333 $h^{-1}$ corresponds to an $SRT_{min}$ of 3.0 h (Horiuchi J. I., Shimizu T., Tada K., Kanno T., Kobayashi M., (2002) Selective production of organic acids in anaerobic acid reactor by pH control. *Bioresource Technol* 82, 209-13).

However, high dilution rates result in a marked decrease in biomass content in the reactor due to severe cell washout and system failure (Wu, S. Y., Hung, C. H., Lin, C. Y., Lin, P. J., Lee, K. S., Lin, C. N., Chang, F. Y. And Chang, J. S. (2008) HRT-dependent hydrogen production and bacterial community structure of mixed anaerobic microflora in suspended, granular and immobilized sludge systems using glucose as the carbon substrate. *Int. J. Hydrogen Energy* 33, 1542-1549). Since acetone-butanol-ethanol (ABE) fermentation utilizes the same bacterial groups that are used for biohydrogen, the process also suffers from biomass washout. Therefore, to resolve biomass washout in ABE fermentation, most of studies in the literature and full-scale applications have utilized batch or fed-batch reactors.

Decoupling of SRT from HRT in hydrogen bioreactors has been achieved by using biofilms on several media including synthetic plastic media and treated anaerobic granular sludge (Das, D., Khanna, N., Veziroglu, T. N., (2008) Recent developments in biological hydrogen production processes. *Chem Ind. and Chem. Eng.* 14 (2), 57-67), activated carbon, expanded clay and loofah sponge (Chang, J. S., Lee, K. S., and Lin, P. J., (2002) Biohydrogen production with fixed-bed bioreactors. *Int. J. Hydrogen Energy* 27 (11/12), 1167-1174), glass beads (Zhang, H., Mary, A. B., Bruce, E. L., (2006) Biological hydrogen production by *clostridium acetobutylicum* in an unsaturated flow reactor. *Water Research* 40, 728-734) and membranes (Vallero, M. V. G., Lettinga, G., and Lens, P. N. L., (2005) High rate sulfate reduction in a submerged anaerobic membrane bioreactor (SAMBaR) at high salinity. *J. Membr. Sci.* 253(1/2), 217-232). Problems with the development of methanogenic biofilms on the carrier media adversely impact process stability, which is critical for sustained hydrogen production. Moreover, membranes have not shown many advantages in terms of volumetric hydrogen yield and are also prone to fouling in such a reductive environment.

A biohydrogenator system provided in WO2010/085893 is intended to address two limitations for sustained biological hydrogen production: contamination of the microbial hydrogen-producing cultures with methane-producing cultures and low bacterial yield of hydrogen-producers. In that system, a gravity settler is used after a hydrogen reactor for decoupling SRT from HRT through sludge. The system disclosed includes a CSTR for biological hydrogen production, followed by a gravity settler positioned downstream of the CSTR, the combination of which forms the biohydrogenator. The biomass concentration in the hydrogen reactor is kept at the desired range through biomass recirculation from the bottom of the gravity settler and/or biomass wastage from the gravity settler's underflow. This prior art biohydrogenator is described to increase hydrogen yield from sugar and carbohydrate based wastes from 1.6 to 3.2 mol $H_2$/mol glucose while producing VFAs primarily acetate as the residual soluble metabolite. Although that represents an improvement over previous systems, this biohydrogenator is still subject to the limitations common to dark fermentation processes: the inhibition of hydrogen production by the accumulation of fermentation end-products. The production and accumulation of acetic and butyric acids results in lower hydrogen yields and a total undissociated acid concentration of 19 mM initiated solventogenesis. Different strains of *Clostridium* produce different ratios of end-products thus affecting their hydrogen-producing potential. The elimination of butyric acid formation and the increased production of acetic acid would provide for increased hydrogen yield from glucose. Although acetate production would increase hydrogen yield to 4 mol of hydrogen per mole of glucose, this is still not enough for the process to be an economically viable alternative to existing hydrogen production methods.

Another biohydrogen production process is the electrohydrogenesis process. In an electrogenesis process, exoelectrogenic bacteria are able to release electrons exogenously (outside the cell) to solid substrates (i.e. a carbon electrode), allowing electricity to be produced in a reactor called a microbial fuel cell (MFC). The oxidation reaction generated by the bacteria at the anode is sustained through the production of water at the cathode from electrons and protons released by the bacteria, and oxygen. The electrohydrogenesis process is similar except that a small potential must be added into the circuit and no oxygen is used at the cathode. Thus, hydrogen gas is evolved at the cathode in a reactor called a microbial electrolysis cell (MEC). The process has also been referred to as a bacterial electrolysis cell (BEC) and a bioelectrochemically assisted microbial reactor (BEAMR): Liu, H., Grot, S., Logan, B. E., (2005) Electrochemically assisted microbial production of hydrogen from acetate. *Environ. Sci. Technol.*, 39, 4317-4320; Rozendal, R. A., Buisman, C. J. N., Bio-Electrochemical Process for Producing Hydrogen. International Publication No. WO 2005/005981; and Rozendal, R. A., Hamelers, H. V. M., Euverink, G. J. W., Metz, S. J.; Buisman, C. J. N. (2006), Principle and perspectives of hydrogen production through biocatalyzed electrolysis. *Int. J. Hydrogen Energy*, 31, 1632-1640. The BEAMR process differs from MFC with respect to loss of hydrogen due to its diffusion from the cathode chamber through the cation exchange membrane (CEM) into the anode chamber. In addition, in the BEAMR process there is no potential for loss of substrate resulting from aerobic growth of bacteria due to oxygen diffusion into the anode chamber from the cathode chamber. Electrohydrogenesis processes are coupled with and dependent on an upstream dark fermentation process (i.e. two completely separate process stages). The advantages of a separate electrohydrogenesis process were evaluated in Liu et al. (2005), Rozendal & Buisman (2005), and Rozendal et al. (2006).

The limitations of batch methods for ABE fermentation are recognized in the literature. Widely reported problems with dark fermentation reactors in the literature include microbial shifts, metabolic shifts, biomass washouts, repeated systems failure, sustainability, low hydrogen yields, methanogens growth and methane production as opposed to hydrogen. With all the aforementioned problems, researchers have moved on to the MEC approach and other solutions as described below.

The effects of pH control on the process of acetone/butanol/ethanol (ABE) production in batch cultures of *Clostridium acetobutylicum* XY16 have been investigated (Ting Guo, T., Sun, B., Jiang, M., Wu, H., Du, T., Tang, Yan., Wei, P., Ouyang, P., (2012) Enhancement of butanol production and reducing power using a two-stage controlled-pH strategy in batch culture of *Clostridium acetobutylicum* XY16. *World J Microbiol Biotechnol* 28, 2551-2558). Based on observed acid- and solvent-forming rates in batch fermentation at different pH values, a two-stage controlled-pH strategy was developed in which the pH was shifted from 5.5 to 4.9 after a dry cell weight of 0.5 g/L was achieved. By applying this strategy, increases in ABE concentration and increases in the ratio of NADH/NAD$^+$ were observed.

A two stage chemostat system integrated with liquid-liquid extraction of solvents produced in a first stage was applied to optimization of continuous acetone-butanol-ethanol (ABE) fermentation (Bankar, S. B., Survase, S. A., Singhal, R. S., Granström, T. (2012) Continuous two stage acetone-butanol-ethanol fermentation with integrated solvent removal using *Clostridium acetobutylicum* B 5313. *Bioresource Technology* 106, 110-116). Minimized end product inhibition by butanol and subsequently enhanced glucose utilization and solvent production were observed in continuous cultures of *Clostridium acetobutylicum* B 5313. During continuous two-stage ABE fermentation, sugarcane bagasse was used as the cell holding material for the both stages and liquid-liquid extraction was performed using an oleyl alcohol and decanol mixture. Increased production of acetone, butanol, and ethanol was observed as compared to the single stage chemostat. Increased glucose utilization was also observed as compared to the single stage chemostat.

Development of a continual flow system by the former Soviet Union is reviewed in Zverlov, V. V., Berezina, O., Velikodvorskaya, V. A., and Schwarz, W. H. (2006) Bacterial acetone and butanol production by industrial fermentation in the Soviet Union: use of hydrolyzed agricultural waste for biorefinery. *Appl Microbiol Biotechnol* 71: 587-597. Two major improvements of AB fermentation from biomass were developed by the Soviet Union: (1) a continual flow process which had great advantages over the batch mode, and (2) use of agricultural waste material by hydrolyzing the hemicelluloses (this extended the amount of raw material for production). To increase overall site production, parallel batteries of reactors connected in series were used. This enabled truly continuous substrate preparation and truly continuous distillation and this batch process can be termed "continual" fermentation (as opposed to "continuous" fermentation). $H_2$, $CO_2$, acetone, butanol, ethanol, and vitamin B12 were produced by AB fermentation of agricultural waste materials (e.g. corn cobs, sunflower seeds, etc.) combined with molasses and wheat or rye flour.

Thus, an improved process is desired which would address at least some of these problems.

SUMMARY

It is an object of the present disclosure to obviate or mitigate at least one disadvantage of previous methods and systems for production of hydrogen, methane, volatile fatty acids, or alcohols from organic material.

The method disclosed herein may be implemented through a system comprising a biohydrogenator including continuously stirred reactor (CSTR) for acetone-butanol-ethanol (ABE) fermentation of organic material. The ABE fermentation results in products including for example acetone, butanol, ethanol, acetic acid, butyric acid, hydrogen gas, and/or carbon dioxide. Hydrogen gas and carbon dioxide are recovered from the CSTR. A gravity settler is downstream of the CSTR. The biomass concentration in the CSTR reactor is kept at the desired range through biomass recirculation from the bottom of the gravity settler and/or biomass wastage from the gravity settler's underflow. A separation process is used to separate further biomass from the acetone, butanol, ethanol, acetic acid, butyric acid, etc., which are recovered. The biomass is provided to a biomethanator for the production of methane gas.

In a preferred embodiment, the present method for producing hydrogen, methane, volatile fatty acids, and alcohols from organic material, comprises the steps of
   introducing organic material and microorganisms into a completely mixed bioreactor for breaking down the organic material into products including $H_2$, $CO_2$, volatile fatty acids, and alcohols;
   recovering at least a portion of the $H_2$ and of the $CO_2$ from the completely mixed bioreactor;
   recovering at least a portion of a first liquid effluent from the completely mixed bioreactor, the first liquid effluent including at least a portion of the microorganisms, the volatile fatty acids, and the alcohols;

introducing at least a portion of the first liquid effluent into a gravity settler for separating at least a portion of the first liquid effluent into a first biomass including at least a portion of the microorganisms and a second liquid effluent including at least a portion of the volatile fatty acids, the alcohols and the microorganisms;

introducing at least a portion of the second liquid effluent into a separation module for separating at least a portion of the second liquid effluent into a second biomass including at least a portion of the microorganisms and a third liquid effluent including at least a portion of the volatile fatty acids and the alcohols;

recovering at least a portion of the third liquid effluent; and providing a recovered biomass by recovering at least a portion of the first biomass, the second biomass, or both, and introducing the recovered biomass into a biomethanator for production of $CH_4$ and $CO_2$.

Preferably, the method includes the further step of providing at least a portion of the first biomass into the completely mixed bioreactor to maintain a concentration of microorganisms in the completely mixed bioreactor at a preselected value. The method also preferably includes the step of controlling the pH of the completely mixed bioreactor, the biomethanator, or both, preferably by adding pH adjustment compounds to the completely mixed bioreactor, the biomethanator, or both. The pH of the completely mixed bioreactor is preferably maintained within a range of 3 to 6.8. The method may also include the step of controlling a temperature of the completely mixed bioreactor, the biomethanator, or both. The temperature of the completely mixed bioreactor and the biomethanator is preferably maintained at a temperature range from about 200° C. to about 700° C., preferably about 25° C. to about 37° C.

Microorganisms useful in the present invention include one or more of the species selected from the group consisting of *Clostridium* species, such as *C. butyricum, C. beijerinckii, C. acetobutyricum* and *C. bifermentants, Enterobacter* species, such as *Enterobacter aerogenes, Bacillus* species such as *B. megaterium, B. thuringiensis,* and *R. sphaeroides*.

Preferably, the completely mixed bioreactor is a reactor selected from the group consisting of a single continuously stirred tank reactor, a multi-stage continuously stirred tank reactor, an up-flow anaerobic sludge blanket reactor, an expanded bed granular sludge blanket reactor, a down-flow anaerobic granular media reactor, an up-flow anaerobic granular media reactor, an anaerobic baffled tank reactor, an anaerobic migrating blanket reactor, and an anaerobic fluidized bed bioreactor.

In another preferred embodiment, the present system for producing hydrogen, methane, volatile fatty acids, and alcohols from organic material, comprises:
 a biomethanator comprising:
  a completely mixed bioreactor for receiving microorganisms and the organic material to be broken down into products including $H_2$, $CO_2$, volatile fatty acids and alcohols, and a first liquid effluent including at least a portion of the microorganisms, the volatile fatty acids, and the alcohols;
  a gravity settler in fluid communication with the completely mixed bioreactor for receiving the first liquid effluent and separating the first liquid effluent into a settled out first biomass including at least a portion of the microorganisms and a second liquid effluent including at least a portion of the volatile fatty acids, the alcohols and the microorganisms;
  a separation module for separating at least a portion of the second liquid effluent into a second biomass including at least a portion of the microorganisms and a third liquid effluent including at least a portion of the volatile fatty acids and the alcohols; and
  a biomethanator in fluid communication with the gravity settler, the separation module, or both, for receiving at least a portion of the first biomass, the second biomass, or both, for production of $CH_4$ and $CO_2$.

The system may further comprise means for feeding the first biomass from the gravity settler to the completely mixed bioreactor for maintaining a concentration of microorganisms in the completely mixed bioreactor at a preselected value. Preferably, the system also includes means for disposing of the first biomass from the gravity settler. The system may also include a means for feeding the first biomass from the gravity settler to the biomethanator for maintaining a concentration of microorganisms in the biomethanator at a preselected value. Preferably, the system includes a dispenser for dispensing chemicals for pH adjustment into the completely mixed bioreactor, the biomethanator, or both. The system preferably further comprises a storage tank in fluid communication with the gravity settler and the biomethanator, wherein the storage tank is downstream of the gravity settler and upstream of the biomethanator, for adjusting loading rates of liquids entering the biomethanator. Most preferably, the storage tank is downstream of the separation module.

The system may also include a dispenser for dispensing chemicals for pH adjustment into at least one of the completely mixed bioreactor, the biomethanator and the storage tank.

Moreover, the system preferably includes a temperature controller for controlling a temperature of at least one of the completely mixed bioreactor, the biomethanator, and the storage tank.

The completely mixed bioreactor is preferably a reactor selected from the group consisting of a single continuously stirred tank reactor, a multi-stage continuously stirred tank reactor, an up-flow anaerobic sludge blanket reactor, an expanded bed granular sludge blanket reactor, a down-flow anaerobic granular media reactor, an up-flow anaerobic granular media reactor, an anaerobic baffled tank reactor, an anaerobic migrating blanket reactor, and an anaerobic fluidized bed bioreactor.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figure.

DETAILED DESCRIPTION

Figure 1:
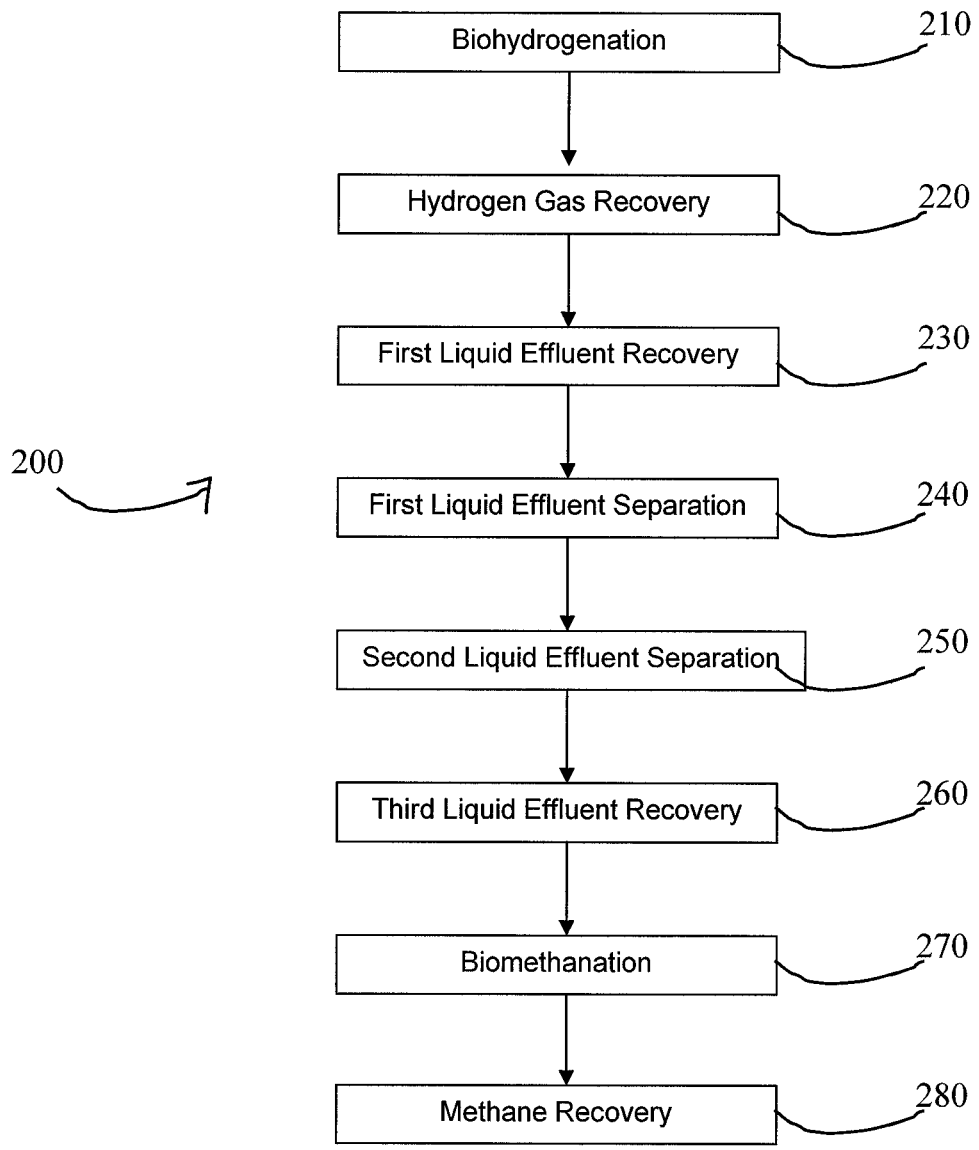
FIG. 1 is a flow diagram of a process for producing hydrogen gas, carbon dioxide, methane, volatile fatty acids, alcohols, and methane from organic biomass.

Generally, the present disclosure provides a method and integrated system for the production of chemicals including hydrogen gas, methane, carbon dioxide, acetone, ethanol, butanol, acetic acid, propionic acid, and butyric acid from organic material. A downstream gravity settler is integrated into the system after the CSTR. The method includes the application of acetone-butanol-ethanol (ABE) fermentation and methanogenesis and integrates a second stage anaerobic digestion process. Embodiments of the method and system are disclosed herein. However, the disclosed embodiments are merely exemplary, and the method and system may be embodied in many various and alternative forms.

As used herein, the terms "about" and "approximately" are used in conjunction with ranges of dimensions, concentrations, temperatures, or other physical or chemical properties and characteristics. Use of these terms is meant to cover slight variations that may exist in the upper and lower limits of the ranges of properties and characteristics.

As used herein, the term "completely mixed bioreactor" means a vessel including a mechanism for agitating the contents of the vessel (e.g. by hydraulic agitation, mechanical agitation, etc.) for use with microorganisms in suspension and a growth media, (e.g. a growth media comprised of nutrients such as organic carbon, nitrogen-containing compounds, phosphorous-containing compounds, and trace mineral solutions, etc.). A continuously stirred reactor (CSTR) is an example of a completely mixed bioreactor.

As used herein, the term "biomethanator" means a vessel used for anaerobic conversion of organic material to methane and carbon dioxide. Biomethanators include, for example, single or multi-stage CSTRs, an up-flow anaerobic sludge blanket reactor, wherein fluid added to the reactor flows upwards through an anaerobic, compacted bed of granular sludge, an expanded bed granular sludge blanket reactor, wherein fluid added to the reactor flows upwards through an anaerobic, expanded bed of granular sludge, a down-flow or up-flow anaerobic granular media reactor, an anaerobic baffled tank reactor, an anaerobic migrating blanket reactor, anaerobic fluidized bed bioreactors, etc.

As used herein, the term "microorganisms" means microorganisms capable of fermenting organic material under anaerobic (not microaerobic) conditions to produce hydrogen or methane, carbon dioxide, and a variety of organic acids and alcohols. Species of microorganisms within this term may include, for example, one or combination of various *Clostridium* species such as *C. butyricum, C. beijerinckii, C. acetobutyricum* and *C. bifermentants, Enterobacter* species such as *Enterobacter aerogenes, Bacillus* species such as *megaterium, thuringiensis*, and other anaerobic bacteria (e.g. *Rhodobacter sphaeroides*).

As used herein, the term "organic material" refers to material with carbon and hydrogen in its molecular structure, for example alcohols, ketones, aldehydes, fatty acids, esters, carboxylic acids, ethers, carbohydrates, proteins, lipids, polysaccharides, monosaccharide, cellulose, nucleic acids, etc. Organic material may be present for example, in waste (e.g. industrial waste streams), organic fluid streams, biomass, etc.

Process

FIG. 1 is a flow diagram of a process 200 for producing hydrogen gas, carbon dioxide, methane, volatile fatty acids, and alcohols from organic biomass. The process 200 includes a biohydrogenation step 210, a hydrogen gas recovery step 220, a first liquid effluent recovery step 230, a first liquid effluent separation step 240, a second liquid effluent separation step 250, a third liquid effluent recovery step 260, a biomethanation step 270, and a methane recovery step 280. The steps 210, 220, 230, 240, 250, 260, 270, 280 may be carried out in a continuous fashion where some or all of the steps 210, 220, 230, 240, 250, 260, 270, 280 are being performed simultaneously and continuously, in contrast with a batch approach where the steps 210, 220, 230, 240, 250, 260, 270, 280 would be carried out sequentially.

In the biohydrogenation step 210, organic material and microorganisms are provided into a completely mixed bioreactor (e.g. the completely mixed bioreactor 22 of FIG. 2) for breaking down the organic material into products including $H_2$, $CO_2$, volatile fatty acids, and alcohols. In the hydrogen gas recovery step 220, at least a portion of the $H_2$ and of the $CO_2$ is recovered from the completely mixed bioreactor. In the first liquid effluent recovery step 230, at least a portion of a first liquid effluent is recovered from the completely mixed bioreactor, the first liquid effluent including at least a portion of the microorganisms, the volatile fatty acids, and the alcohols.

In the first liquid effluent separation step 240, at least a portion of the first liquid effluent is fed into a gravity settler (e.g. the gravity settler 24 of FIG. 2) for separating at least a portion of the first liquid effluent into a first biomass including at least a portion of the microorganisms and a second liquid effluent including at least a portion of the volatile fatty acids, the alcohols and the microorganisms. Although other separators, such as membrane separators are known, they are capital intensive and much harder to operate. In the second liquid effluent separation step 250, at least a portion of the second liquid effluent is fed to a separation module (e.g. the separation module 30 of FIG. 2) for separating at least a portion of the second liquid effluent into a second biomass including at least a portion of the microorganisms and a third liquid effluent including at least a portion of the volatile fatty acids and the alcohols. At least a portion of the third liquid effluent is recovered in the third liquid effluent recovery step 260.

In the biomethanation step 270, at least a portion of the first biomass, the second biomass, or both, is recovered and provided to a biomethanator (e.g. the biomethanator 40 of FIG. 2) for producing $CH_4$ and $CO_2$. At least a portion of the $CH_4$ and $CO_2$ is recovered in the methane recovery step 280.

The first liquid effluent separation step 240 may include recirculating at least a portion of the first biomass to the completely mixed bioreactor to maintain a concentration of microorganisms in the completely mixed bioreactor at a preselected value.

The second liquid effluent separation step 250 may include application of a variety of separation process, for example membrane solvent separation.

The pH range may be controlled in the completely mixed bioreactor during the biohydrogenation step 210. For example, the pH range may be kept within a range of 3 to 6.8 depending on the desired end products.

The pH range may be controlled in the biomethanator during the biomethanation step 270. The temperature may be controlled in the completely mixed bioreactor during the biohydrogenation step 210. For example, the temperature may be kept within a range of about 25° C. to about 37° C.

The temperature may be controlled in the biomethanator during the biomethanation step 270. For example, the temperature may be kept within a range of about 25° C. to about 37° C.

The microorganisms useful for application in the system of the present application include *Clostridium* species, such as *C. butyricum, C. beijerinckii, C. acetobutyricum* and *C. bifermentants, Enterobacter* species, such as *Enterobacter aerogenes, Bacillus* species such as *B. megaterium, B. thuringiensis*, and *R. sphaeroides*.

System

Figure 2:
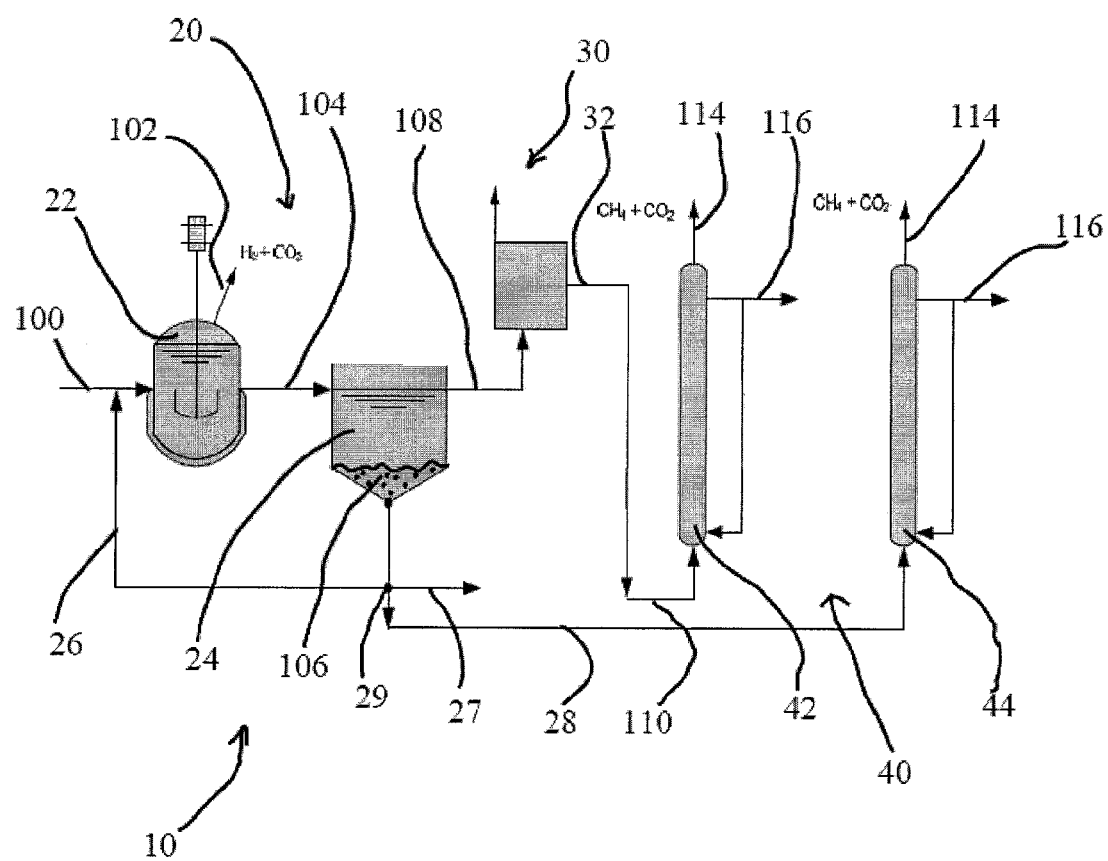
FIG. 2 is a schematic of a system for employing the method of FIG. 1.

FIG. 2 is a schematic of a system 10 for producing hydrogen gas, carbon dioxide, methane, volatile fatty acids, and alcohols from organic material. Further products produced by the system 10 may include acetone, ethanol, butanol, acetic acid, propionic acid, and butyric acid. The system 10 includes a biohydrogenator 20, a separation module 30, and a biomethanator 40.

The biohydrogenator 20 includes a completely mixed bioreactor 22 having an inlet for receiving organic material 100 into the completely mixed bioreactor 22. Microorganisms are added to the completely mixed bioreactor 22 to break down the organic material 100, producing $H_2$ and $CO_2$ 102 and a first liquid effluent 104. The first liquid effluent 104 may include, for example, microorganisms, volatile fatty acids (e.g. acetic acid, propionic acid, butyric acid, etc.), alcohols (e.g. ethanol, butanol, etc.), acetone, etc.

The biohydrogenator 20 further includes a gravity settler 24 downstream of the completely mixed bioreactor 22 and in fluid communication with the completely mixed bioreactor 22 for receiving the first liquid effluent 104 from the completely mixed bioreactor 22. In the gravity settler 24, the first liquid effluent 104 settles into a first biomass 106 and a second liquid effluent 108. The second liquid effluent 108 may include, for example, microorganisms, volatile fatty acids (e.g. acetic acid, propionic acid, butyric acid, etc.), alcohols (e.g. ethanol, butanol, etc.), acetone, etc.

A biohydrogenator conduit 26 provides fluid communication from the bottom of the gravity settler 24 to the completely mixed bioreactor 22 for recirculating the first biomass 106 from the gravity settler 24 to the completely mixed bioreactor 22. An output conduit 27 from the bottom of the gravity settler 24 is for discharging and disposal the first biomass 106. A first biomethanator conduit 28 provides fluid communication from the bottom of the gravity settler to the biomethanator 40 for circulating the first biomass 106 from the gravity settler 24 to the biomethanator 40. A valve 29 allows selection of flow through one or more of the biohydrogenator conduit 26, the output conduit 27, and the first biomethanator conduit 28.

The separation module 30 is in fluid communication with the gravity settler 24 for receiving the second liquid effluent 108. In the separation module 30, the second liquid effluent 108 may be separated into a second biomass 110 and a third liquid effluent 112 by application of a separation process. The third liquid effluent 112 may include, for example, volatile fatty acids (e.g. acetic acid, propionic acid, butyric acid, etc.), alcohols (e.g. ethanol, butanol, etc.), acetone, etc. A second biomethanator conduit 32 provides fluid communication from the separation module 30 to the biomethanator 40 for circulating the second biomass 110 from the separation module 30 to the biomethanator 40.

The biomethanator 40 is downstream of, and in fluid communication with, the gravity settler 24, the separation module 30, or both. The biomethanator 40 may receive biomass from the biohydrogenator 20, the separation module 30, or both, for being broken down into $CH_4$ and $CO_2$ 114, and a liquid waste 116 containing residual organics and microorganisms.

The biomethanator 40 may include a first biomethanator vessel 42, a second biomethanator vessel 44, or both. The first biomethanator vessel 42 is in fluid communication with the first biomethanator conduit 28 for receiving the first biomass 106 from the gravity settler 24. The second biomethanator vessel 44 is in fluid communication with the second biomethanator conduit 32 for receiving the second biomass 110 from the separation module 30.

The system 10 may include a storage tank (not shown) in fluid communication with the gravity settler 24 and the biomethanator 40. The storage tank is downstream of the gravity settler 24 and upstream of the biomethanator 40 for adjusting loading rates of the liquids entering the biomethanator 40. The system 10 may include a dispenser (not shown) for dispensing chemicals into the storage tank for adjusting alkalinity and pH of the liquid in the storage tank.

The system 10 may include a temperature controller (not shown) for controlling the temperature in the completely mixed bioreactor 22, in the biomethanator 40, or both. A typical temperature range in which the temperature of the contents of both the completely mixed bioreactor 22 and biomethanator 40 is maintained is between about 25° C. and about 37° C.

The system 10 may include a dispenser (not shown) for dispensing nutrients and pH adjustment compounds into the completely mixed bioreactor. The nutrients may include, for example, nitrogen containing compounds, phosphorous containing compounds, trace metals including iron, manganese, magnesium, calcium, cobalt, zinc, nickel, copper, etc. The pH adjustment compounds may include, for example, soda ash, sodium bicarbonate, sodium hydroxide, calcium hydroxide, magnesium hydroxide, nitric acid, hydrochloric acid, etc.

Operation

The system 10 may be applied to practice an embodiment of the process 200. The organic material 100 enters the completely mixed bioreactor 22 and is broken down microbiologically by hydrogen producing microorganisms, resulting in products including the $H_2$ and $CO_2$ 102, and the first liquid effluent 104. The $H_2$ and $CO_2$ 102, are emitted from the completely mixed bioreactor 22 and recovered. The first liquid effluent 104 flows to the gravity settler 24.

In the gravity settler 24, at least a portion of the microorganisms settle to the bottom of the gravity settler 24, resulting in the first biomass 106 and the second liquid effluent 108. The first biomass 106 may be recirculated to the completely mixed bioreactor 22, provided to the biomethanator 40, disposed of, or a combination thereof. The second liquid effluent 108 flows into the separation module 30.

In the separation module 30, at least a portion of the second liquid effluent 108 settles into a second biomass 110 and a third liquid effluent 112. The third liquid effluent 112 is emitted from the separation module 30 and recovered. The second biomass 110 may be provided to the biomethanator 40. Providing the second biomass 110 to the completely mixed bioreactor is also possible, but not necessary in the presence of a recycle stream from the gravity settler 24.

The first biomass 106 is provided to the first biomethanator vessel 42 through the first biomethanator conduit 28. The second biomass 110 is provided to the second biomethanator vessel 44 through the second biomethanator conduit 34. In the biomethanator 40, the first biomass 106, the second biomass 110, or both, are broken down microbiologically, resulting in production of the $CH_4$ and $CO_2$ 114. The $CH_4$ and $CO_2$ 114 are emitted from the biomethanator 40 and recovered. The liquid waste 116 is discharged from the biomethanator 40, recirculated into the biomethanator 40, or both.

To gain a better understanding of the invention described herein, the following examples are set forth. It should be understood that these examples are for illustrative purposes only. Therefore, they should not limit the scope of this invention in anyway.

EXAMPLES

Material and Methods
Systems Set Up and Operations
A system comprised a CSTR for ABE production (2 L working volume), followed by an uncovered gravity settler (volume 8 L) i.e. open to atmosphere, for the decoupling of SRT from the HRT. Details of the operational conditions for the three runs are listed in Table 1. In order to enrich ABE producing bacteria and hinder the methane producing microorganisms, the sludges were treated at 70° C. for 30 min.

TABLE 1

Operating conditions

| Parameter | Units | OLR (1) | OLR (2) | OLR (3) |
|---|---|---|---|---|
| Glucose concentration | g/L | 10 | 30 | 60 |
| HRT | hr | 12 | 12 | 12 |
| Feed flow rate | L/d | 4 | 4 | 4 |
| OLR | g COD/$L_{reactor}$ · d | 21 | 64 | 128 |
| Recycle flow rate | L/d | 2 | 4 | 6 |
| SRT | hr | 51 | 62 | 59 |
| pH | | 4.0-5.5 | 4.0-5.5 | 4.0-5.5 |
| NaHCO3 | g/L | 2 | 5 | 8 |
| F/M | g COD/g VSS · d | 1.1 | 1.9 | 3.2 |

Operating Conditions and Medium Composition
The operating condition of the three organic loading rates (OLRs) is presented in Table 1. The system was started by inoculating a preheated anaerobic digested sludge which was collected from anaerobic digester at St Marys Waste Water Treatment Plant (WWTP), ON, Canada, and used as seed. The sludge contains a mixture of *clostridium* bacteria and other bacterial species. The seed was heated at 70° for 30 min before used; the inoculation period was about 2 weeks using the operation conditions of OLR-1. The system was seeded with 1.5 liters of sludge and started up in a continuous mode with the feed containing glucose at different concentrations as presented in Table 1. The feed medium composition is presented in Table 2.

TABLE 2

Nutrient medium composition used in the feed

| Nutrient | Concentration (g/L) |
|---|---|
| Yeast extract | 1 |
| $KH_2PO_4$ | 0.5 |
| $NH_4Cl$ | 2 |
| $MgSO_4·7H_2O$ | 0.2 |
| $MnSO_4·H_2O$ | 0.01 |
| $FeSO_4·7H_2O$ | 0.01 |
| $ZnCl_2$ | 0.05 |
| $H_3BO_3$ | 0.05 |
| $CuCl_2$ | 0.03 |
| $Mo_7(NH_4)_6O_{24}$ | 0.5 |
| $AlCl_3$ | 0.05 |
| $CoCl_2·6H_2O$ | 0.05 |
| $NiCl_2$ | 0.05 |

* 1 mL of the nutrient medium was added to each 1 L substrate for OLR (1) and 2 ml was used for OLRs (2) and (3).

There was no sludge wastage from the clarifier throughout the operation, and the values of SRTs presented in Table 1 represent the average. The pH in the reactor was adjusted at pH 5.5±0.2 every day in the morning using KOH, and then was allowed to drop naturally (due to the production of acids and ABE) without any control. At the end of each cycle (24 hr), the pH was monitored and it was about 3.5-4.2. The average pH reported in this report is the pH at the middle of the 24 hr cycle.

Analytical Methods
ABE concentrations were analysed using Hewlett Packard 5890 gas chromatograph equipped with a spilt injection port, capillary column (DB-VRX 30 m×0.32 mm I.D., 1.8 um film thickness), PID (Photoionization detector, 11.7 eV) and a Varian Genesis headspace autosampler. The detection limits for these compounds are found to be in the range of 1-10 mg/L. Helium gas was used as a carrier gas (3.5 ml/min). The initial temperature of the column was 40° C., increasing to 100° C. at the rate of 10° C./min, and then held constant at the final temperature of 100° C. for 1 min. Injector and detector temperatures were 150° C. and 65° C., respectively. For analysis, samples are collected in glass vials, capped with a tegrabond teflon septa, and stored in a 4° C. refrigerator until analyzed. Prior to gas chromatography (GC)-PID analyses, the vials are uncapped and 14.5 mL of samples were transferred to a 22 mL auto sampler vial with a crimp top seal. Then, the samples are then placed in the auto sampler carousel.

Volatile fatty acids (VFAs) which includes acetate, propionate, n-butyrate, n-valerate, iso-butyrate, and iso-valerate were quantified using a gas chromatography (Model: Hewlett Packard HP 5890 Series II) equipped with a Nukol fused-silica capillary column and flame ionization detector (FID). Helium gas was used as a carrier gas. The initial temperature of the column was 110° C., increasing to 195° C. at the rate of 8° C./min, and then held constant at the final temperature of 195° C. for 9 min. Injector and detector temperatures were 220° C. and 280° C., respectively. Prior to GC-FID analyses, the liquid samples were acidified to pH 2 using 1 N phosphoric acid, and then filtered using 0.2 μm membrane filter (DISMIC-25 HP, Toyo Roshi Kaisha Ltd., Japan).

The pH values were measured with a pH Meter (Model 420A, Orion Research Inc., USA). The total and soluble chemical oxygen demand (TCOD and SCOD) concentrations were analyzed with Hach COD analysis kits (reagent 20-1,500 mg/L COD range, Hach Company, USA), according to the Hach method. The liquid samples were filtered with 0.45 μm membrane (RK-02915-14, Cole-Parmer, USA) for collecting soluble samples. Total suspended solids (TSS) and volatile suspended solids (VSS) concentrations were measured according to the Standard Methods (APHA, 1998). Glucose was analyzed by anthrone-sulfuric acid method (Dubois et al., 1956).

Results

Figure 3:
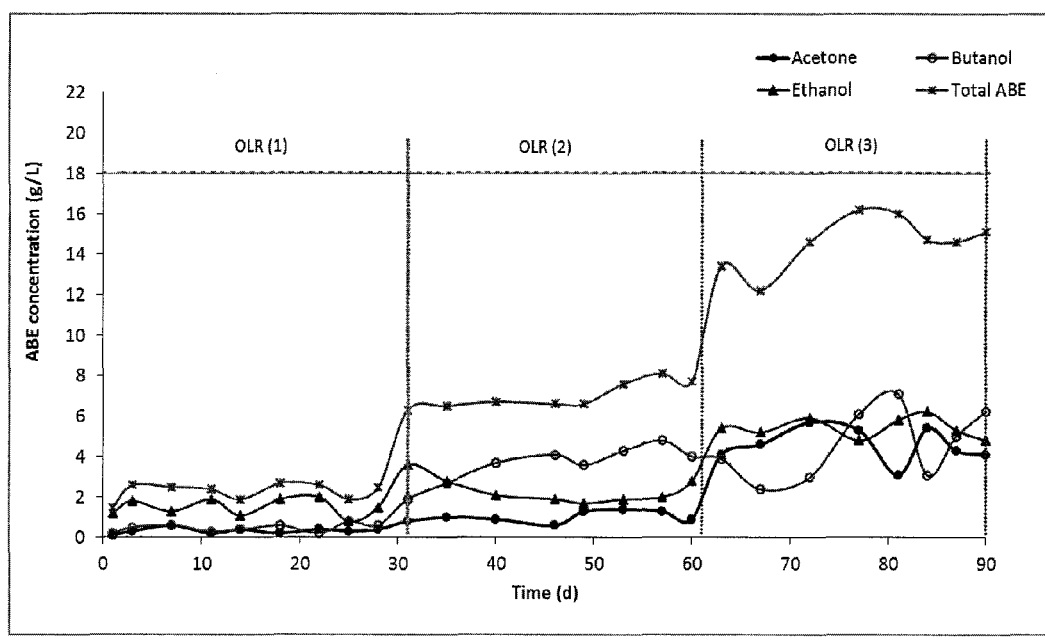
FIG. 3 is a graph depicting diurnal variation for ABE concentration at different OLRs.
Figure 4:
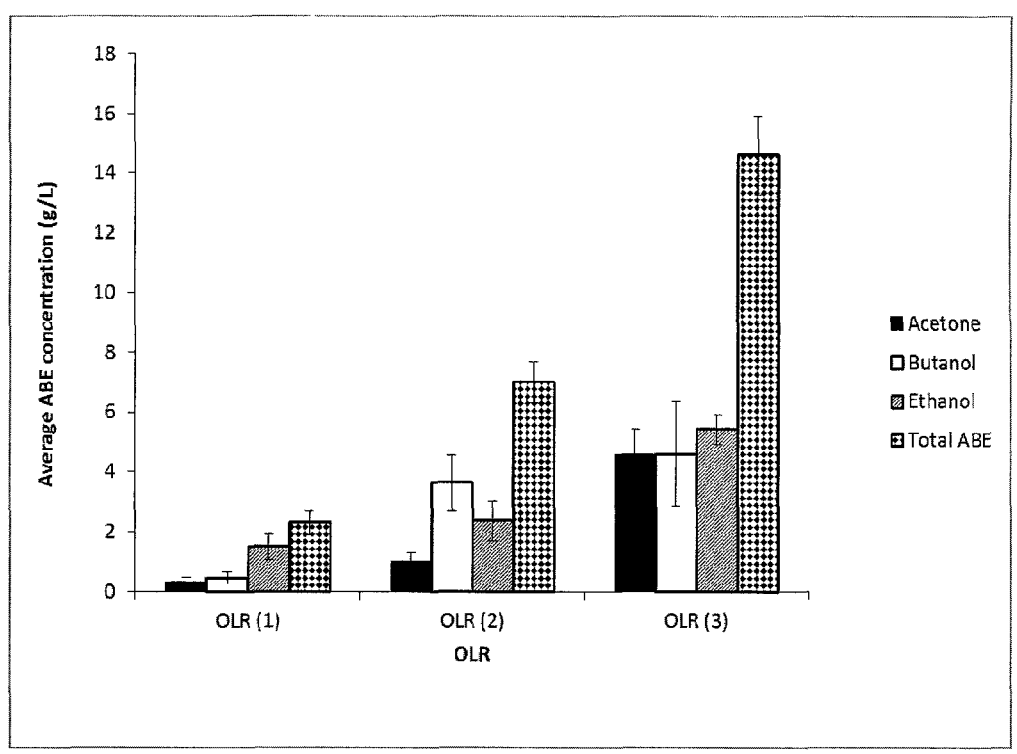
FIG. 4 is a graph depicting average ABE concentrations at different OLRs.

FIG. 3 shows the diurnal variation of ABE concentration at the three OLRs of 21, 64, and 128 g COD/Lreactor.d which were corresponding to glucose concentrations of 10, 30, and 60 g/L, respectively. After the system reached a steady-state (steady-state required about 3-5 days after the start-up), the system was run for about 30 days for each OLR. As shown in FIG. 3, the system showed stable ABE production during the experimental period reflected by low coefficient of variation of less than 10%. The concentrations of the individual components increased with increasing the OLR. The butanol concentration of 3.6 g/L was the predominant component at OLR-2 compared to 1 g/L acetone and 2.4 g/L ethanol. The average concentrations of the individual components at OLR-3 were acetone 4.6 g/L, butanol 4.6 g/L, and ethanol 5.4 g/L. Furthermore, the total ABE concentrations increased with increasing the OLR, the average ABE concentrations of 2.3, 7.0, and 14.6 g ABE/L were achieved for OLRs of 21, 64, and 128 g COD/Lreactor.d, respectively, see FIG. 4.

Figure 5:
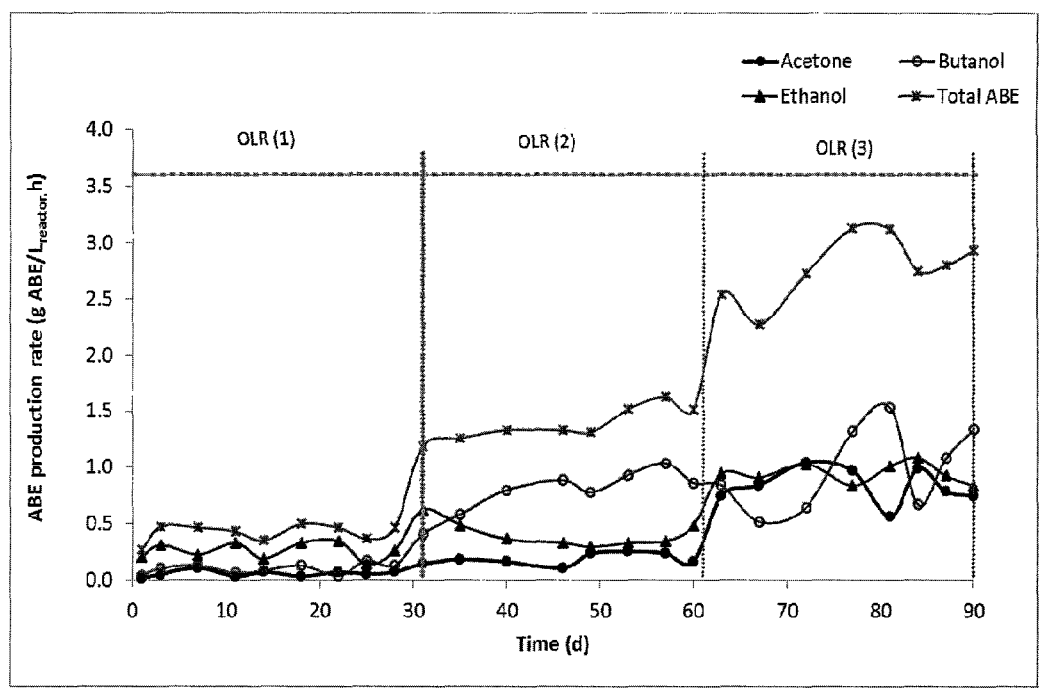
FIG. 5 is a graph depicting diurnal variation for ABE production rate at different OLRs.
Figure 6:
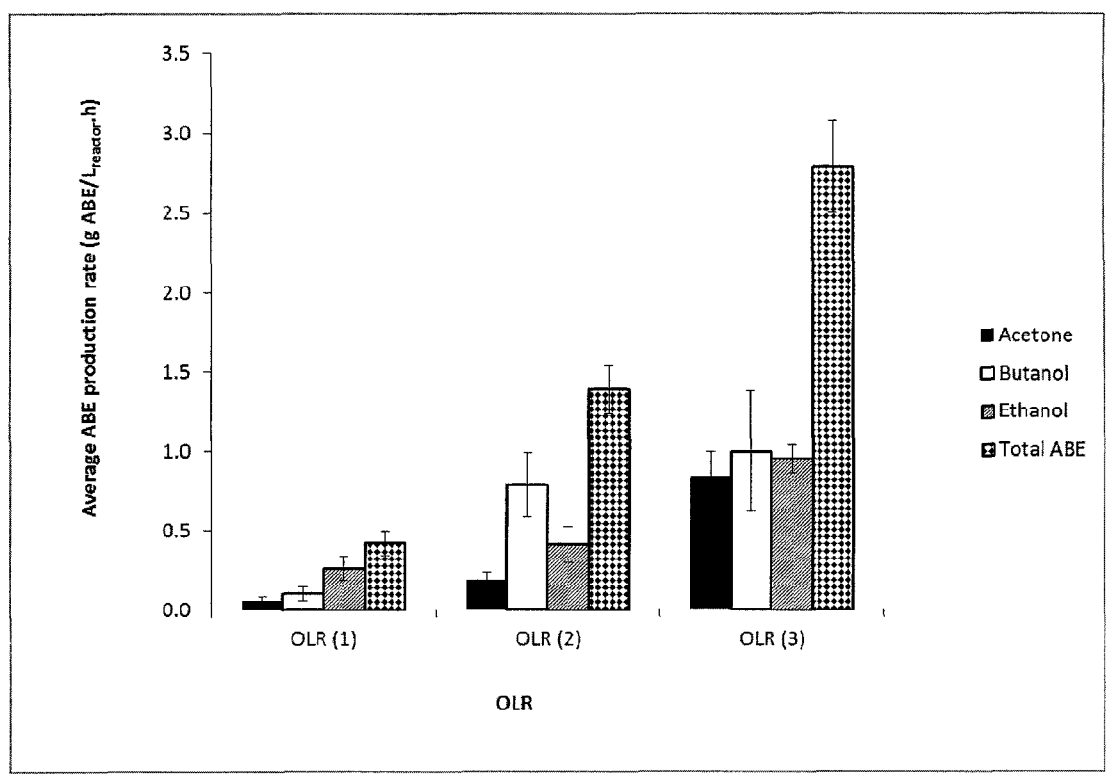
FIG. 6 is a graph depicting average ABE production rates at different OLRs.

FIG. 5 shows the diurnal variation of ABE production rate at the three OLRs. As depicted in the Figure, a stable production rate was observed at the different OLRs. The average ABE production rate of 0.4, 1.4, and 2.8 g ABE/Lreactor.h were achieved at OLRs 1-3, respectively, see FIG. 6. The maximum ABE production rate of 3.2 g ABE/Lreactor.h was observed at OLR-3 which was much higher than the production rates reported previously reported. The biomass concentration in the fermenter is an important parameter that affects the system stability and production rate. As depicted in Table 3, the average biomass concentrations of 4.9, 8.3, and 10 g/L in the reactor were achieved at OLRs 1-3, respectively.

TABLE 3

Liquid quality parameters of the reactor samples at the three OLRs

| Param- | | OLR (1) | | OLR (2) | | OLR (3) | |
|---|---|---|---|---|---|---|---|
| eter | Units | Average | STD | Average | STD | Average | STD |
| TCOD | g/L | 12.3 | 0.8 | 30.9 | 2.1 | 56.4 | 2.8 |
| SCOD | g/L | 7.4 | 0.7 | 23.5 | 2.6 | 50.2 | 3.3 |

TABLE 3-continued

Liquid quality parameters of the reactor samples at the three OLRs

| Param- | | OLR (1) | | OLR (2) | | OLR (3) | |
|---|---|---|---|---|---|---|---|
| eter | Units | Average | STD | Average | STD | Average | STD |
| TSS | g/L | 5.3 | 0.4 | 8.8 | 0.2 | 10.4 | 0.2 |
| VSS | g/L | 4.9 | 0.4 | 8.3 | 0.2 | 10.0 | 0.2 |

Data in the Table are the average and STD of eight samples.

Figure 7:
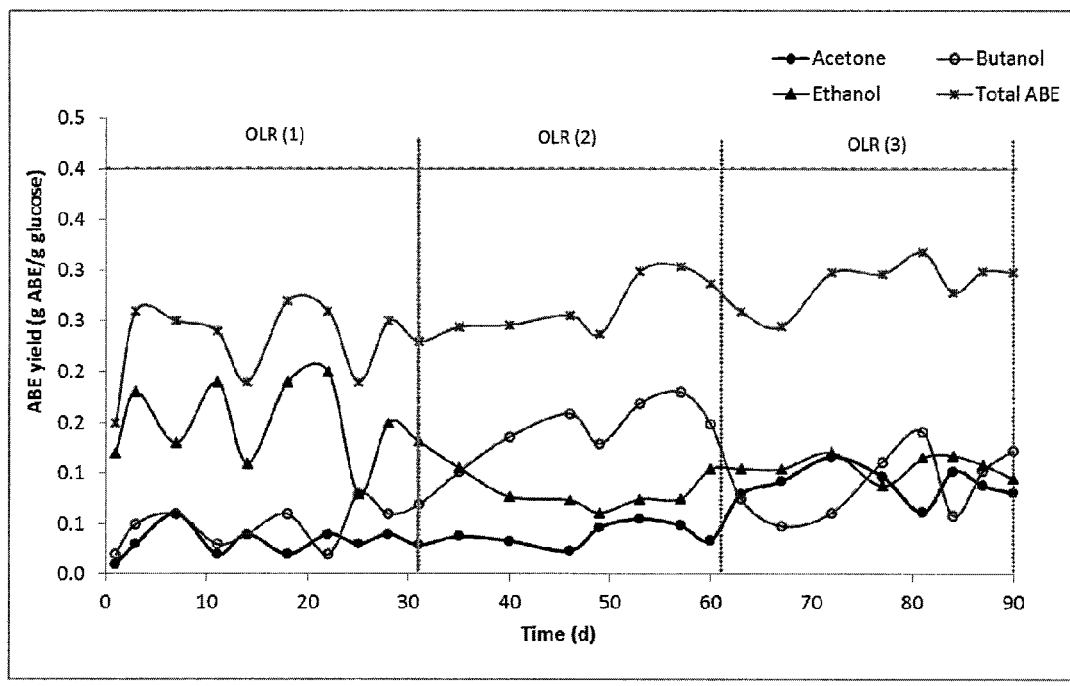
FIG. 7 is a graph depicting diurnal variation for ABE yields at different OLRs.
Figure 8:
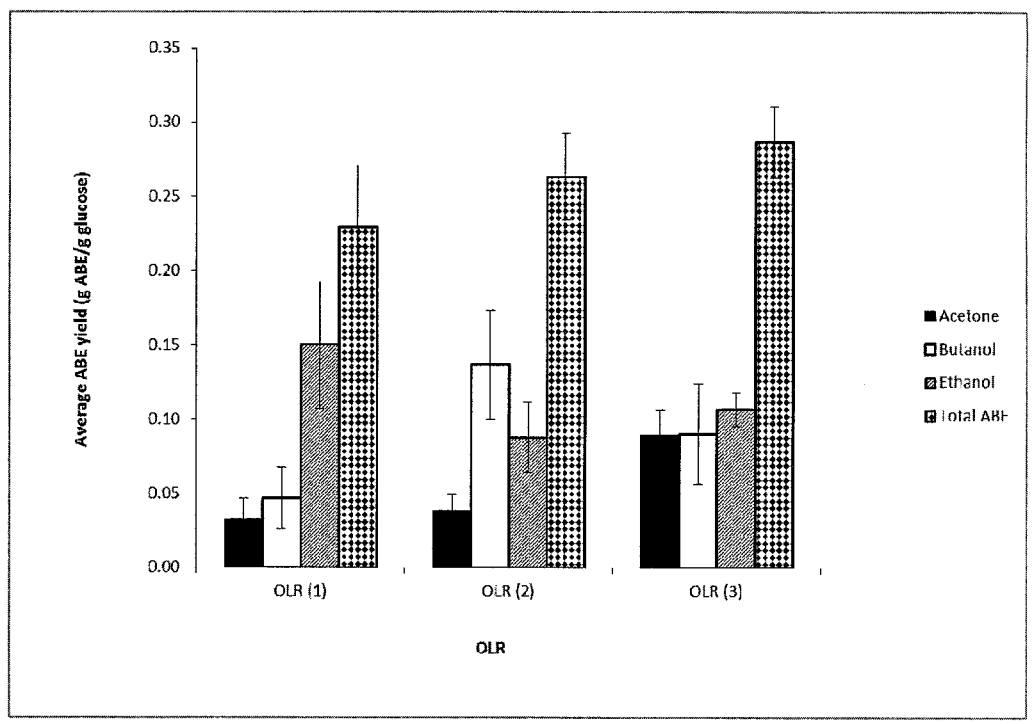
FIG. 8 is a graph depicting average ABE yields at different OLRs.

The diurnal variations of ABE yields at the three OLRs are presented in FIG. 7. As depicted in the Figure, a stable steady ABE yield was observed at the three OLRs. The average ABE yields of 0.23, 0.26, and 0.29 g ABE/g glucose converted (FIG. 8).

Figure 9:
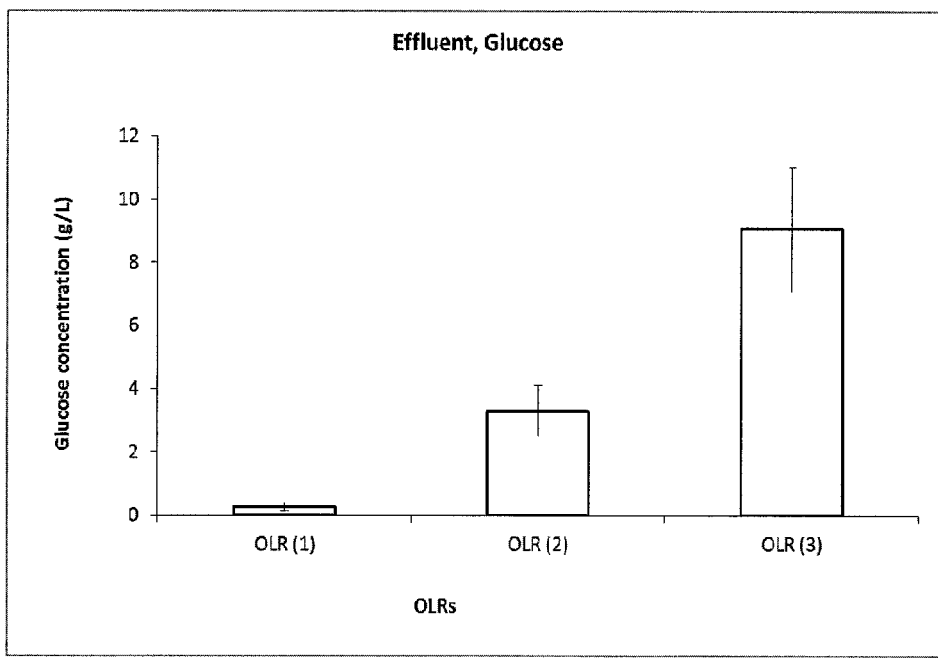
FIG. 9 is a graph depicting average effluent glucose at different OLRs.

FIG. 9 shows the glucose concentration in the effluent, the average glucose concentrations of 0.3, 3.3, and 9.1 g/L which were corresponding to conversion efficiencies of 97%, 89%, and 85% at the three OLRs 1-3, respectively. The effluent SCOD of 8, 26.8, and 52.3 g/L were observed at the three OLRs 1-3, respectively (Table 4).

TABLE 4

Liquid quality parameters of the effluent samples at the three OLRs

| Param- | | OLR (1) | | OLR (2) | | OLR (3) | |
|---|---|---|---|---|---|---|---|
| eter | Units | Average | STD | Average | STD | Average | STD |
| Glucose | g/L | 0.3 | 0.1 | 3.3 | 0.8 | 9.1 | 2.0 |
| TCOD | g/L | 9.5 | 0.4 | 30.0 | 1.1 | 54.2 | 1.8 |
| SCOD | g/L | 8.0 | 0.6 | 26.8 | 1.8 | 52.3 | 3.4 |
| TSS | g/L | 1.5 | 0.1 | 1.9 | 0.2 | 2.3 | 0.1 |
| VSS | g/L | 1.2 | 0.1 | 2 | 0.3 | 2 | 0.1 |
| pH | | 4.3 | 0.3 | 4.2 | 0.4 | 4.2 | 0.6 |
| Alk | mg CaCO3/L | 1780 | 180 | 2780 | 340 | 2960 | 250 |

Data in the Table are the average and STD of eight samples

As shown in Table 5, the TVFAs concentrations in the effluent were 2.2, 4.7, and 5.5 g COD/L at the three OLRs 1-3, respectively. The main VFAs components in the effluent were acetic, propionic, and butyric acids.

TABLE 5

Summary of the steady state data at the three OLRs

| Param- | | OLR (1) | | OLR (2) | | OLR (3) | |
|---|---|---|---|---|---|---|---|
| eter | Units | Average | STD | Average | STD | Average | STD |
| Acetone | g/L | 0.3 | 0.1 | 1.0 | 0.3 | 4.6 | 0.9 |
| Butanol | g/L | 0.5 | 0.2 | 3.6 | 0.9 | 4.6 | 1.7 |
| Ethanol | g/L | 1.5 | 0.4 | 2.4 | 0.7 | 5.4 | 0.5 |
| Total ABE | g/L | 2.3 | 0.4 | 7.0 | 0.7 | 14.6 | 1.3 |
| ABE yield | g ABE/g glucose | 0.23 | 0.04 | 0.26 | 0.03 | 0.29 | 0.02 |
| ABE production rate | g ABE/$L_{reactor}$ · h | 0.4 | 0.08 | 1.4 | 0.15 | 2.8 | 0.29 |
| Acetic acid | g COD/L | 0.50 | 0.20 | 2.30 | 0.50 | 2.50 | 1.00 |
| Propionic acid | g COD/L | 0.6 | 0.2 | 0.5 | 0.4 | 1.0 | 0.8 |
| Butyric acid | g COD/L | 1.1 | 0.6 | 2 | 0.9 | 2 | 1 |
| TVFAs | g COD/L | 2.2 | 0.5 | 5 | 1.2 | 6 | 2.1 |

Data in the Table are the average and STD of eight samples

Figure 10:
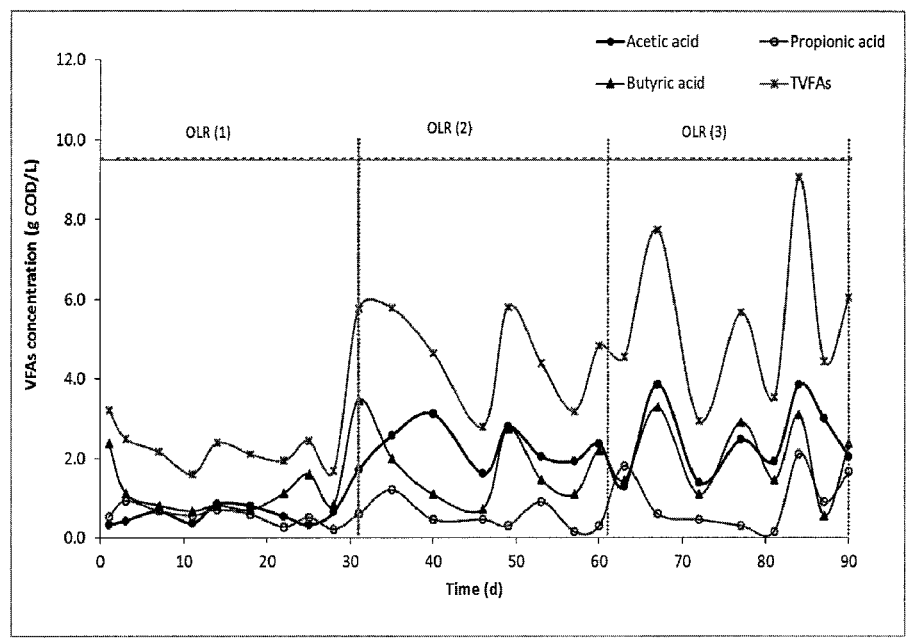
FIG. 10 is a graph depicting diurnal variation for VFAs concentration at different OLRs.
Figure 11:
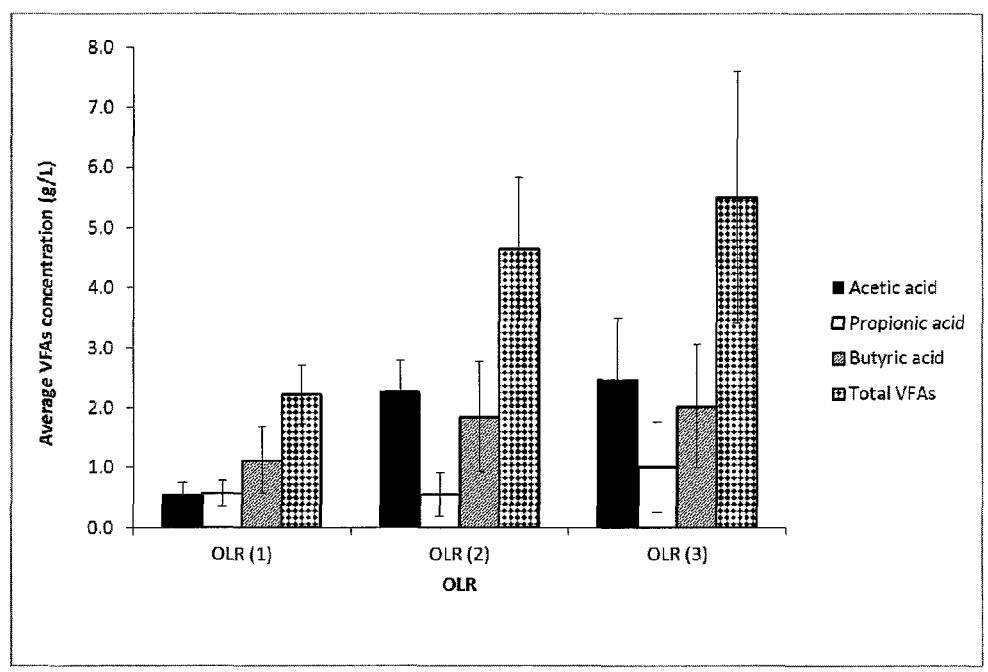
FIG. 11 is a graph depicting average VFAs at different OLRs.

In the OLR-1, the acetic acid was the predominant component. In OLRs 2 and 3, the butyric acid was the predominant acid. The TVFAs in the effluent counted for 11-28% of the effluent SCOD. FIG. 10 depicts diurnal variation for VFAs concentration at different OLRs. FIG. 11 depicts average VFAs at different OLRs As depicted in Tables 4 and 5, the sum of ABE and VFAs counted for 91%, 79%, and 74% of the effluent SCOD at the three OLRs 1-3, respectively.

Figure 12:
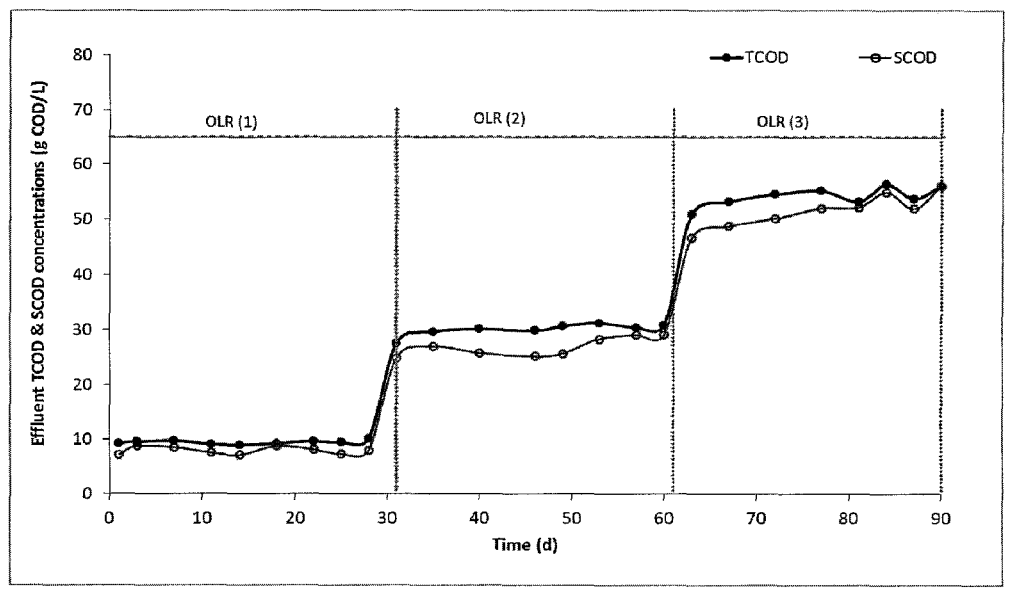
FIG. 12 is a graph depicting diurnal variation for effluent TCOD and SCOD concentrations at different OLRs.

FIG. 12 depicts diurnal variation for effluent TCOD and SCOD concentrations at different OLRs.

Figure 13:
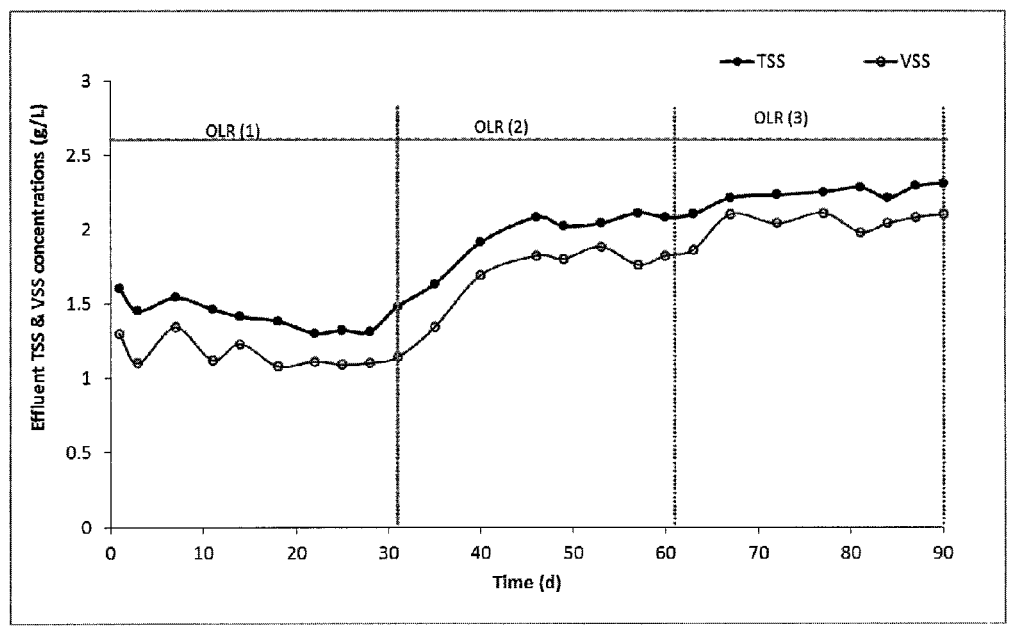
FIG. 13 is a graph depicting diurnal variation for effluent TSS and VSS concentrations at different OLRs.

FIG. 13 depicts diurnal variation for effluent TSS and VSS concentrations at different OLRs.

Figure 14:
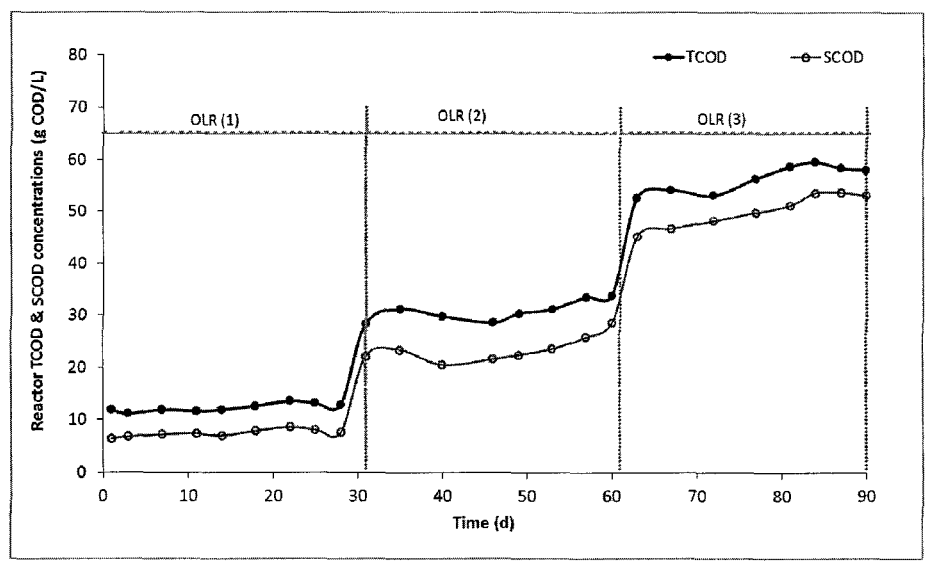
FIG. 14 is a graph depicting diurnal variation for reactor TCOD and SCOD concentrations at different OLRs.

FIG. 14 depicts diurnal variation for reactor TCOD and SCOD concentrations at different OLRs.

Figure 15:
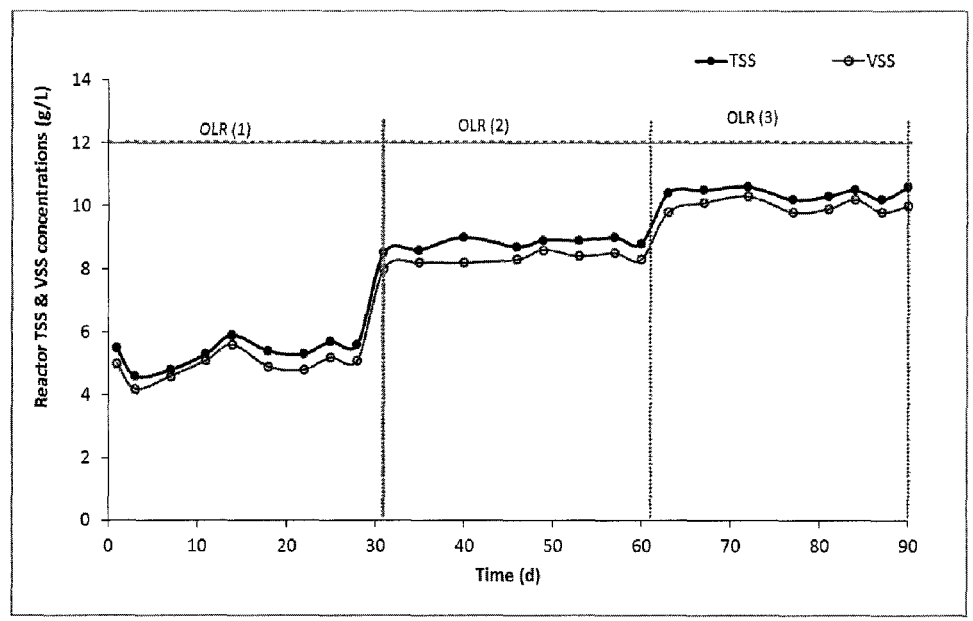
FIG. 15 is a graph depicting diurnal variation for reactor TSS and VSS concentrations at different OLRs.

FIG. 15 depicts diurnal variation for reactor TSS and VSS concentrations at different OLRs.

Figure 16:
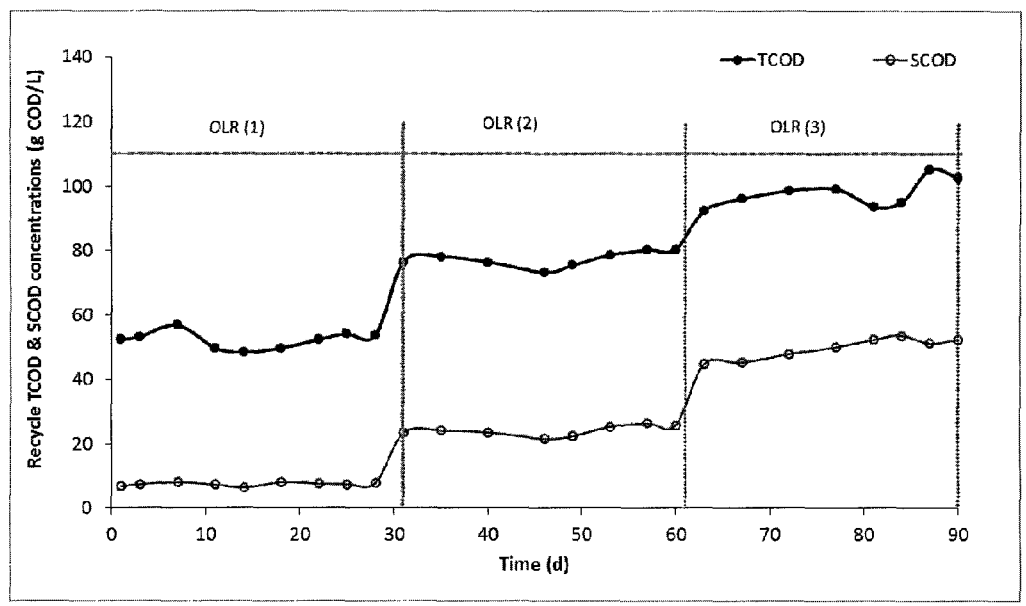
FIG. 16 is a graph depicting diurnal variation for recycle TCOD and SCOD concentrations at different OLRs.

FIG. 16 depicts diurnal variation for recycle TCOD and SCOD concentrations at different OLRs.

Figure 17:
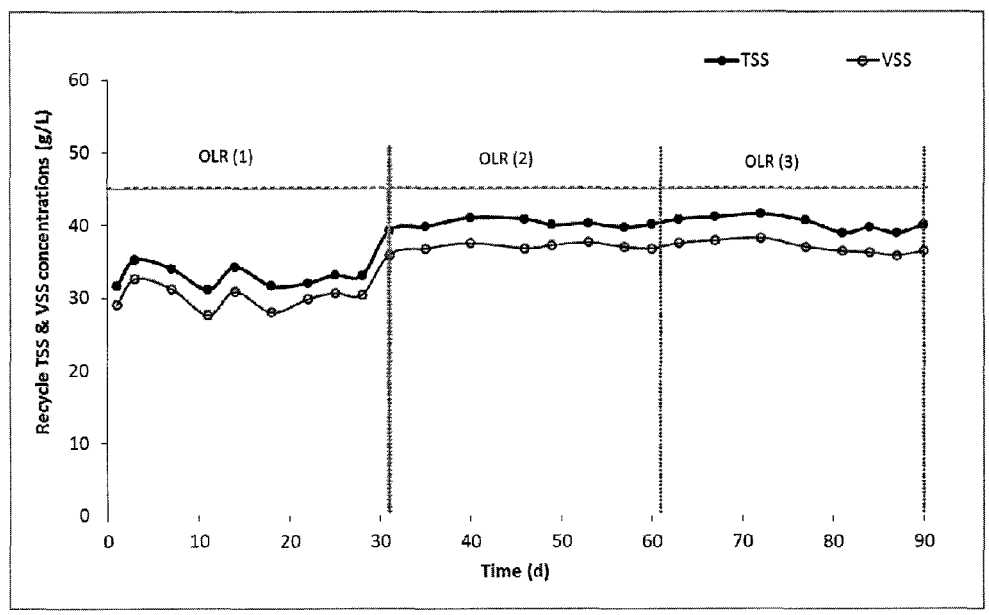
FIG. 17 is a graph depicting diurnal variation for recycle TSS and VSS concentrations at different OLRs.

FIG. 17 depicts diurnal variation for recycle TSS and VSS concentrations at different OLRs.

As shown in Table 6, the biomass concentration in the recycle line (i.e. settled biomass) of 30 g/L was achieved at OLR-1, this concentration increased to 37 g/L at OLRs 2 and 3.

TABLE 6

Liquid quality parameters of the recycle samples at the three OLRs

| Parameter | Units | OLR (1) Average | STD | OLR (2) Average | STD | OLR (3) Average | STD |
|---|---|---|---|---|---|---|---|
| TCOD | g/L | 52.2 | 2.6 | 77.3 | 2.5 | 97.9 | 4.5 |
| SCOD | g/L | 7.5 | 0.6 | 24.1 | 1.7 | 49.7 | 3.4 |
| TSS | g/L | 32.9 | 1.4 | 40.1 | 0.6 | 40.2 | 1.0 |
| VSS | g/L | 30.0 | 1.6 | 37.0 | 0.5 | 36.9 | 0.9 |
| ZSV | m/d | 160 | 8 | 186 | 9 | 198 | 7 |
| SVI | mL/g | 130 | 11 | 90 | 8 | 80 | 5 |

Data in the Table are the average and STD of eight samples.

To evaluate the settling characteristics of the biomass, both zone settling velocity (ZSV) and sludge volume index (SVI) were analyzed. As shown in Table 6, the ZSV ranged from 160-198 m/d and SVI from 80 to 130 mL/g. The settleability of the ABE producers was considered to be superior to activated sludge since SVI of 100 mL/g and ZSV of 100 m/d are considered typical for good settling activated sludge. Furthermore, the low effluent VSS concentrations of 1.16, 1.66, and 2.04 g/L that were observed at the OLRs 1-3, respectively, demonstrating the good settleability of the ABE producers.

The data in Table 7 depict the COD Mass Balance at the three OLRs tested, and show high COD balance % at the OLRs.

TABLE 7

COD Mass balance at the three OLRs

| OLR | $SCOD_{out}$ mg/L | $VSS_{out}$ mg/L | $H_2$ L/d | $SCOD_{out}$ mg COD/d | $VSS_{out}$ mg COD/d | $H_2$ mg COD/d | COD balance % |
|---|---|---|---|---|---|---|---|
| OLR (1) | 8000 | 1160 | 1.5 | 32000 | 6589 | 1080 | 93 |
| OLR (2) | 26800 | 1660 | 3.4 | 107200 | 9429 | 2448 | 93 |
| OLR (3) | 52300 | 2040 | 7.7 | 209200 | 11587 | 5544 | 88 |

CONCLUSIONS

As shown herein, Acetone-Butanol-Ethanol (ABE) concentrations of 2.3, 7, and 14.6 g/L were achieved at OLRs of 21, 64, and 128 g COD/Lreactor.d, respectively.

The ABE yields of 0.29 total g ABE/g glucose was achieved at OLR of 128 g COD/Lreactor.d.

The ABE production rate increased from 0.4 g ABE/Lreactor.h at OLR of 21 g COD/Lreactor.d to 1.4 and 2.8 g ABE/Lreactor.h at OLRs of 64, and 128 g COD/Lreactor.d, recpectively.

Acetic, propionic, and butyric acids were detected in all phases, the total volatile fatty acids (TVFAs) in the effluent of 2.2, 4.7, and 5.5 g COD/L were observed at OLRs of 21, 64, and 128 g COD/Lreactor.d, respectively.

The glucose concentration in the effluent was less than 0.5 g/L for OLR of 21 g COD/Lreactor.d and increased to about 3.0 and 9.0 g/L for OLRs of 64 and 128 g COD/Lreactor.d, respectively.

The low effluent VSS of 1.2-2 g/L, ZSV of 160-198 mL/d, and SVI of 80-130 mL/g demonstrated the superior settleability of the ABE fermenters.

All references cited herein are incorporated by reference.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

REFERENCES

APHA, 1998. Standard Methods for the Examination of Water and Wastewater, 20th ed., American Public Health Association, Washington D.C., USA.

Bruant, G., Lévesque, M. J., Peter, C., Guiot, S. R., & Masson, L. (2010). Genomic analysis of carbon monoxide utilization and butanol production by *Clostridium carboxidivorans* strain P7T. PloS one, 5(9), e13033.

Du, J., McGraw, A., Lorenz, N., Beitle, R. R., Clausen, E. C., & Hestekin, J. A. (2012). Continuous Fermentation of *Clostridium tyrobutyricum* with Partial Cell Recycle as a Long-Term Strategy for Butyric Acid Production. Energies, 5(8), 2835-2848.

Dubois, M., Gilles, K. A., Hamilton, J. K., Rebers, P. A., Smith, F. (1956). Colorimetric method for determination of sugars and related substances, Anal Chem 28, 350-356.

Ezeji, T. C., Qureshi, N., & Blaschek, H. P. (2013). Microbial production of a biofuel (acetone-butanol-ethanol)

in a continuous bioreactor: impact of bleed and simultaneous product removal. Bioprocess and biosystems engineering, 36(1), 109-116.

Ezeji, T. C., Qureshi, N., & Blaschek, H. P. (2013). Microbial production of a biofuel (acetone-butanol-ethanol) in a continuous bioreactor: impact of bleed and simultaneous product removal. Bioprocess and biosystems engineering, 36(1), 109-116.

Ezeji, T., Qureshi, N., & Blaschek, H. P. (2007). Production of acetone-butanol-ethanol (ABE) in a continuous flow bioreactor using degermed corn and Clostridium beijerinckii. Process biochemistry, 42(1), 34-39.

Gheshlaghi, R. E. Z. A., Scharer, J. M., Moo-Young, M., & Chou, C. P. (2009). Metabolic pathways of clostridia for producing butanol. Biotechnology advances, 27(6), 764-781.

Green, E. M. (2011). Fermentative production of butanol—the industrial perspective. Current opinion in biotechnology, 22(3), 337-343.

Huang, W. D., & Zhang, Y. H. P. (2011). Analysis of biofuels production from sugar based on three criteria: Thermodynamics, bioenergetics, and product separation. Energy & Environmental Science, 4(3), 784-792.

Jiang, M., Chen, J. N., He, A. Y., Wu, H., Kong, X. P., Liu, J. L., Chen, P. (2014). Enhanced acetone/butanol/ethanol production by Clostridium beijerinckii IB4 using pH control strategy. Process Biochemistry, in press (http://dx.doi.org/10.1016/j.procbio.2014.04.017).

Jin, C., Yao, M., Liu, H., Lee, C. F. F., & Ji, J. (2011). Progress in the production and application of n-butanol as a biofuel. Renewable and Sustainable Energy Reviews, 15(8), 4080-4106.

Linggang, S., Phang, L. Y., Wasoh, H., & Abd-Aziz, S. (2013). Acetone-butanol-ethanol production by Clostridium acetobutylicum ATCC 824 using sago pith residues hydrolysate. BioEnergy Research, 6(1), 321-328

Liu, Z., Ying, Y., Li, F., Ma, C., & Xu, P. (2010). Butanol production by Clostridium beijerinckii ATCC 55025 from wheat bran. Journal of industrial microbiology & biotechnology, 37(5), 495-501.

Ni, Y., Xia, Z., Wang, Y., & Sun, Z. (2013). Continuous butanol fermentation from inexpensive sugar-based feedstocks by Clostridium saccharobutylicum DSM 13864. Bioresource technology, 129, 680-685.

Papoutsakis, E. T. (2008). Engineering solventogenic clostridia. Current opinion in biotechnology, 19(5), 420-429.

Parekh, M., Formanek, J., & Blaschek, H. P. (1999). Pilot-scale production of butanol by Clostridium beijerinckii BA101 using a low-cost fermentation medium based on corn steep water. Applied microbiology and biotechnology, 51(2), 152-157.

Qureshi, N., Bowman, M. J., Saha, B. C., Hector, R., Berhow, M. A., & Cotta, M. A. (2012). Effect of cellulosic sugar degradation products (furfural and hydroxymethyl furfural) on acetone-butanol-ethanol (ABE) fermentation using Clostridium beijerinckii P260. Food and Bioproducts Processing, 90(3), 533-540.

Qureshi, N., Ezeji, T. C., Ebener, J., Dien, B. S., Cotta, M. A., & Blaschek, H. P. (2008). Butanol production by Clostridium beijerinckii. Part I: Use of acid and enzyme hydrolyzed corn fiber. Bioresource technology, 99(13), 5915-5922.

Qureshi, N., Saha, B. C., Hector, R. E., Dien, B., Hughes, S., Liu, S., . . . & Cotta, M. A. (2010). Production of butanol (a biofuel) from agricultural residues: Part II—Use of corn stover and switchgrass hydrolysates. Biomass and bioenergy, 34(4), 566-571.

Survase, S. A., van Heiningen, A., & Granström, T. (2012). Continuous bio-catalytic conversion of sugar mixture to acetone-butanol-ethanol by immobilized Clostridium acetobutylicum DSM 792. Applied microbiology and biotechnology, 93(6), 2309-2316.

Thang, V. H., Kanda, K., & Kobayashi, G. (2010). Production of acetone-butanol-ethanol (ABE) in direct fermentation of cassava by Clostridium saccharoperbutylacetonicum N1-4. Applied biochemistry and biotechnology, 161(1-8), 157-170.

Van Hecke, W., Vandezande, P., Claes, S., Vangeel, S., Beckers, H., Diels, L., & De Wever, H. (2012). Integrated bioprocess for long-term continuous cultivation of Clostridium acetobutylicum coupled to pervaporation with PDMS composite membranes. Bioresource technology, 111, 368-377.

Webb, L. J. (1985). An investigation into the occurrence of sewage fungus in rivers containing papermill effluents—II. Chemical analysis of mill effluents. Water Research, 19(8), 955-959.

What is claimed is:

1. A method for acetone-butanol-ethanol (ABE) fermentation of organic material, comprising the steps of:
    a) conducting an ABE fermentation of the organic material in a completely mixed bioreactor to produce acetone, butanol, ethanol (ABE), volatile fatty acids, $H_2$ and $CO_2$, wherein the ABE fermentation step includes introducing organic material and ABE producing microorganisms into a completely mixed bioreactor and controlling a pH of the completely mixed bioreactor to maintain the pH at 3.5-5.5 for breaking down the organic material into products including acetone butanol, ethanol (ABE), volatile fatty acids, $H_2$ and $CO_2$;
    b) recovering at least a portion of the $H_2$ and of the $CO_2$ from the completely mixed bioreactor;
    c) maintaining a biomass concentration in the completely mixed bioreactor, wherein the step of maintaining a biomass concentration includes recovering a first liquid effluent from the completely mixed bioreactor, the first liquid effluent including at least a portion of the microorganisms, the volatile fatty acids, and the ABE;
    d) introducing the first liquid effluent into a gravity settler for separating at least a portion of the first liquid effluent into a first biomass including at least a portion of the microorganisms and a second liquid effluent including at least a portion of the volatile fatty acids, the ABE and the microorganisms;
    e) recirculating at least a portion of the first biomass into the completely mixed bioreactor to maintain a concentration of microorganisms in the completely mixed bioreactor at a preselected value;
    f) producing methane in a biomethanator from the first biomass extracted from the first liquid effluent of the ABE fermentation step, wherein the step of producing methane further includes introducing at least a portion of the second liquid effluent into a separation module for separating at least a portion of the second liquid effluent into a second biomass, including at least a portion of the microorganisms, that is broken down to generate methane and a third liquid effluent including at least a portion of the volatile fatty acids and the ABE;
    h) recovering the volatile fatty acids and ABE from the third liquid effluent; and
    i) providing a recovered biomass by recovering at least a portion of the first biomass, the second biomass, or both, and introducing the recovered biomass into the biomethanator for the production of $CH_4$ and $CO_2$.

2. The method of claim 1, further comprising controlling a pH of the biomethanator.

3. The method of claim 2, wherein controlling the pH comprises adding pH adjustment compounds to the completely mixed bioreactor, the biomethanator, or both.

4. The method of claim 1, further comprising controlling a temperature of the completely mixed bioreactor, the biomethanator, or both.

5. The method according to claim 4, wherein the temperature of the completely mixed bioreactor is maintained at a temperature range from about 25° C. to about 37° C.

6. The method according to claim 4, wherein the temperature of the biomethanator is maintained in a temperature range from about 25° C. to about 37° C.

7. The method according to claim 1, wherein the microorganisms include one or more of the species selected from the group consisting of *Clostridium butyricum, Clostridium beijerinckii, Clostridium acetobutyricum, Clostridium bifermentants, Enterobacter aerogenes, Bacillus megaterium, Bacillus thuringiensis*, and *Rhodobacter sphaeroides*.

8. The method according to claim 1, wherein the completely mixed bioreactor is a reactor selected from the group consisting of a single continuously stirred tank reactor, a multi-stage continuously stirred tank reactor, an up-flow anaerobic sludge blanket reactor, an expanded bed granular sludge blanket reactor, a down-flow anaerobic granular media reactor, an up-flow anaerobic granular media reactor, an anaerobic baffled tank reactor, an anaerobic migrating blanket reactor, and an anaerobic fluidized bed bioreactor.

* * * * *